(12) United States Patent
Fischer et al.

(10) Patent No.: US 6,329,422 B1
(45) Date of Patent: *Dec. 11, 2001

(54) COMPOSITIONS AND METHODS FOR CYSTIC FIBROSIS THERAPY

(75) Inventors: Horst Fischer; Beate Illek, both of Albany, CA (US)

(73) Assignee: Children's Hospital Oakland Research Institute, Oakland, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/174,077

(22) Filed: Oct. 16, 1998

Related U.S. Application Data

(63) Continuation-in-part of application No. 08/951,912, filed on Oct. 16, 1997.

(51) Int. Cl.⁷ ............................ A61K 31/35; A61K 31/21
(52) U.S. Cl. ............................ 514/456; 514/513; 514/851
(58) Field of Search ..................................... 514/456, 513, 514/851

(56) References Cited

U.S. PATENT DOCUMENTS 5,972,995 * 10/1999 Fischer et al. ...................... 514/456

FOREIGN PATENT DOCUMENTS

| 87-105816 | 3/1987 | (JP) . |
| 93-330545 | 9/1993 | (JP) . |
| 94-277493 | 2/1994 | (JP) . |
| 95-135875 | 3/1995 | (JP) . |

OTHER PUBLICATIONS

Brown et al., "Chemical chaperones correct the mutant phenotype of the ΔF508 cystic fibrosis transmembrane conductance regulatory protein," *Cell Stress & Chaperones* 1(2): 117–125, 1996.

Hwang et al., "Genistein potentiates wild–type and ΔF508–CFTR channel activity," *American Journal of Physiology* 273(3, part 1): C988–C998, 1997.

Scott and Cooperstein, "Ascorbic acid stimulates chloride transport in the amphibian cornea," *Investigative Ophtalmology* 14(10): 763–766, 1975.

Smith, "Treatment of cystic fibrosis based on understanding CFTR," *J. Inher. Metab. Dis.* 18: 508–516, 1995.

Rubenstein et al., "In Vitro Pharmacologic Restoration of CFTR–mediated Chloride Transport with Sodium 4–Phenylbutyrate in Cystic Fibrosis Epithelial Cells," *J. Clin. Invest.* 100(10): 2457–2465, 1997.

Sheppard et al., "Mutations in CFTR associated with mild–disease–form CI channels with altered pore properties," *Nature* 362: 160–164, 1993.

\* cited by examiner

*Primary Examiner*—Gary Geist
*Assistant Examiner*—Howard Owens
(74) *Attorney, Agent, or Firm*—Seed IP Law Group PLLC

(57) ABSTRACT

Compositions and methods for therapy of cystic fibrosis and other conditions are provided. The compositions comprise one or more compounds such as flavones and/or isoflavones capable of stimulating chloride transport in epithelial tissues. Therapeutic methods involve the administration (e.g., orally or via inhalation) of such compositions to a patient afflicted with cystic fibrosis and/or another condition responsive to stimulation of chloride transport.

32 Claims, 19 Drawing Sheets

SEQUENCE LISTING

<160> NUMBER OF SEQ ID NOS: 6

<210> SEQ ID NO 1
<211> LENGTH: 6129
<212> TYPE: DNA
<213> ORGANISM: Homo sapiens

<400> SEQUENCE: 1

| | | | | | |
|---|---|---|---|---|---|
| aattggaagc | aaatgacatc | acagcaggtc | agagaaaaag | ggttgagcgg | caggcaccca | 60 |
| gagtagtagg | tctttggcat | taggagcttg | agcccagacg | gccctagcag | ggaccccagc | 120 |
| gcccgagaga | ccatgcagag | gtcgcctctg | gaaaaggcca | gcgttgtctc | caaacttttt | 180 |
| ttcagctgga | ccagaccaat | tttgaggaaa | ggatacagac | agcgcctgga | attgtcagac | 240 |
| atataccaaa | tcccttctgt | tgattctgct | gacaatctat | ctgaaaaatt | ggaaagagaa | 300 |
| tgggatagag | agctggcttc | aaagaaaaat | cctaaactca | ttaatgccct | tcggcgatgt | 360 |
| tttttctgga | gatttatgtt | ctatggaatc | tttttatatt | tagggaagt | caccaaagca | 420 |
| gtacagcctc | tcttactggg | aagaatcata | gcttcctatg | acccggataa | caaggaggaa | 480 |
| cgctctatcg | cgatttatct | aggcataggc | ttatgccttc | tctttattgt | gaggacactg | 540 |
| ctcctacacc | cagccatttt | tggccttcat | cacattggaa | tgcagatgag | aatagctatg | 600 |
| tttagtttga | tttataagaa | gactttaaag | ctgtcaagcc | gtgttctaga | taaaataagt | 660 |
| attggacaac | ttgttagtct | cctttccaac | aacctgaaca | aatttgatga | aggacttgca | 720 |
| ttggcacatt | tcgtgtggat | cgctcctttg | caagtggcac | tcctcatggg | gctaatctgg | 780 |
| gagttgttac | aggcgtctgc | cttctgtgga | cttggtttcc | tgatagtcct | tgccctttt | 840 |
| caggctgggc | tagggagaat | gatgatgaag | tacagagatc | agagagctgg | gaagatcagt | 900 |
| gaaagacttg | tgattacctc | agaaatgatt | gaaaatatcc | aatctgttaa | ggcatactgc | 960 |
| tgggaagaag | caatggaaaa | aatgattgaa | aacttaagac | aaacagaact | gaaactgact | 1020 |
| cggaaggcag | cctatgtgag | atacttcaat | agctcagcct | tcttcttctc | agggttcttt | 1080 |
| gtggtgtttt | tatctgtgct | tccctatgca | ctaatcaaag | gaatcatcct | ccggaaaata | 1140 |
| ttcaccacca | tctcattctg | cattgttctg | cgcatggcgg | tcactcggca | atttccctgg | 1200 |
| gctgtacaaa | catggtatga | ctctcttgga | gcaataaaca | aaatacagga | tttcttacaa | 1260 |
| aagcaagaat | ataagacatt | ggaatataac | ttaacgacta | cagaagtagt | gatggagaat | 1320 |
| gtaacagcct | tctgggagga | gggatttggg | gaattatttg | agaaagcaaa | acaaaacaat | 1380 |
| aacaatagaa | aaacttctaa | tggtgatgac | agcctcttct | tcagtaattt | ctcacttctt | 1440 |
| ggtactcctg | tcctgaaaga | tattaatttc | aagatagaaa | gaggacagtt | gttggcggtt | 1500 |
| gctggatcca | ctggagcagg | caagacttca | cttctaatga | tgattatggg | agaactggag | 1560 |
| ccttcagagg | gtaaaattaa | gcacagtgga | agaatttcat | tctgttctca | gttttcctgg | 1620 |
| attatgcctg | gcaccattaa | agaaaatatc | atctttggtg | tttcctatga | tgaatataga | 1680 |
| tacagaagcg | tcatcaaagc | atgccaacta | gaagaggaca | tctccaagtt | tgcagagaaa | 1740 |

```
gacaatatag ttcttggaga aggtggaatc acactgagtg gaggtcaacg agcaagaatt    1800
tctttagcaa gagcagtata caaagatgct gatttgtatt tattagactc tccttttgga    1860
tacctagatg ttttaacaga aaaagaaata tttgaaagct gtgtctgtaa actgatggct    1920
aacaaaacta ggattttggt cacttctaaa atggaacatt taaagaaagc tgacaaaata    1980
ttaattttga atgaaggtag cagctatttt tatgggacat tttcagaact ccaaaatcta    2040
cagccagact ttagctcaaa actcatggga tgtgattctt tcgaccaatt tagtgcagaa    2100
agaagaaatt caatcctaac tgagaccttta caccgtttct cattagaagg atgctcct    2160 gtctcctgga cagaaacaaa aaacaatct tttaaacaga ctggagagtt tggggaaaaa    2220
aggaagaatt ctattctcaa tccaatcaac tctatacgaa aattttccat tgtgcaaaag    2280
actcccttac aaatgaatgg catcgaagag gattctgatg agcctttaga gagaaggctg    2340
tccttagtac cagattctga gcagggagag gcgatactgc ctcgcatcag cgtgatcagc    2400
actggcccca cgcttcaggc acgaaggagg cagtctgtcc tgaacctgat gacacactca    2460
gttaaccaag gtcagaacat tcaccgaaag acaacagcat ccacacgaaa agtgtcactg    2520
gcccctcagg caaacttgac tgaactggat atatattcaa gaaggttatc tcaagaaact    2580
ggcttggaaa taagtgaaga aattaacgaa gaagacttaa aggagtgcct ttttgatgat    2640
atggagagca taccagcagt gactacatgg aacacatacc ttcgatatat tactgtccac    2700
aagagcttaa ttttttgtgct aatttggtgc ttagtaattt ttctggcaga ggtggctgct    2760
tctttggttg tgctgtggct ccttggaaac actcctcttc aagacaaagg gaatagtact    2820
catagtagaa ataacagcta tgcagtgatt atcaccagca ccagttcgta ttatgtgttt    2880
tacatttacg tgggagtagc cgacactttg cttgctatgg gattcttcag aggtctacca    2940
ctggtgcata ctctaatcac agtgtcgaaa attttacacc acaaaatgtt acattctgtt    3000
cttcaagcac ctatgtcaac cctcaacacg ttgaaagcag gtgggattct aatagattc    3060 tccaaagata tagcaatttt ggatgacctt ctgcctctta ccatatttga cttcatccag    3120
ttgttattaa ttgtgattgg agctatagca gttgtcgcag ttttacaacc ctacatcttt    3180
gttgcaacag tgccagtgat agtggctttt attatgttga gagcatattt cctccaaacc    3240
tcacagcaac tcaaacaact ggaatctgaa ggcaggagtc aattttcac tcatcttgtt    3300 acaagcttaa aaggactatg gacacttcgt gccttcggac ggcagcctta ctttgaaact    3360
ctgttccaca aagctctgaa tttacatact gccaactggt tcttgtacct gtcaacactg    3420
cgctggttcc aaatgagaat agaaatgatt tttgtcatct tcttcattgc tgttaccttc    3480
atttccattt taacaacagg agaaggagaa ggaagagttg gtattatcct gactttagcc    3540
atgaatatca tgagtacatt gcagtgggct gtaaactcca gcatagatgt ggatagcttg    3600
atgcgatctg tgagccgagt cttttaagttc attgacatgc caacagaagg taaacctacc    3660
aagtcaacca aaccatacaa gaatggccaa ctctcgaaag ttatgattat tgagaattca    3720
cacgtgaaga aagatgacat ctggccctca ggggccaaa tgactgtcaa agatctcaca    3780
gcaaaataca cagaaggtgg aaatgccata ttagagaaca tttccttctc aataagtcct    3840
ggccagaggg tgggcctctt gggaagaact ggatcaggga agagtacttt gttatcagct    3900
tttttgagac tactgaacac tgaaggagaa atccagatcg atggtgtgtc ttgggattca    3960
ataactttgc aacagtggag gaaagccttt ggagtgatac cacagaaagt atttattttt    4020
tctggaacat ttagaaaaaa cttggatccc tatgaacagt ggagtgatca agaaatatgg    4080
```

-continued

```
aaagttgcag atgaggttgg gctcagatct gtgatagaac agtttcctgg gaagcttgac   4140
tttgtccttg tggatggggg ctgtgtccta agccatggcc acaagcagtt gatgtgcttg   4200
gctagatctg ttctcagtaa ggcgaagatc ttgctgcttg atgaacccag tgctcatttg   4260
gatccagtaa cataccaaat aattagaaga actctaaaac aagcatttgc tgattgcaca   4320
gtaattctct gtgaacacag gatagaagca atgctgaat gccaacaatt tttggtcata    4380
gaagagaaca aagtgcggca gtacgattcc atccagaaac tgctgaacga gaggagcctc   4440
ttccggcaag ccatcagccc ctccgacagg gtgaagctct tccccaccg gaactcaagc    4500 aagtgcaagt ctaagcccca gattgctgct ctgaaagagg agacagaaga gaggtgcaa    4560 gatacaaggc tttagagagc agcataaatg ttgacatggg acatttgctc atggaattgg   4620
agctcgtggg acagtcacct catggaattg gagctcgtgg aacagttacc tctgcctcag   4680
aaaacaagga tgaattaagt ttttttttaa aaagaaaca tttggtaagg ggaattgagg    4740
acactgatat gggtcttgat aaatggcttc ctggcaatag tcaaattgtg tgaaaggtac   4800
ttcaaatcct tgaagattta ccacttgtgt tttgcaagcc agattttcct gaaaacccctt  4860 gccatgtgct agtaattgga aaggcagctc taaatgtcaa tcagcctagt tgatcagctt   4920
attgtctagt gaaactcgtt aatttgtagt gttggagaag aactgaaatc atacttctta   4980
gggttatgat taagtaatga taactggaaa cttcagcggt ttatataagc ttgtattcct   5040
ttttctctcc tctccccatg atgtttagaa acacaactat attgtttgct aagcattcca   5100
actatctcat ttccaagcaa gtattagaat accacaggaa ccacaagact gcacatcaaa   5160
atatgcccca ttcaacatct agtgagcagt caggaaagag aacttccaga tcctggaaat   5220
cagggttagt attgtccagg tctaccaaaa atctcaatat ttcagataat cacaatacat   5280
cccttacctg ggaagggct gttataatct ttcacagggg acaggatggt tcccttgatg    5340
aagaagttga tatgcctttt cccaactcca gaaagtgaca agctcacaga cctttgaact   5400
agagtttagc tggaaaagta tgttagtgca aattgtcaca ggacagccct tctttccaca   5460
gaagctccag gtagagggtg tgtaagtaga taggccatgg gcactgtggg tagacacaca   5520
tgaagtccaa gcatttagat gtataggttg atggtggtat gttttcaggc tagatgtatg   5580
tacttcatgc tgtctacact aagagagaat gagagacaca ctgaagaagc accaatcatg   5640 aattagttt atatgcttct gttttataat tttgtgaagc aaaatttttt ctctaggaaa    5700
tatttatttt aataatgttt caaacatata ttacaatgct gtattttaaa agaatgatta   5760
tgaattacat ttgtataaaa taatttttat atttgaaata ttgactttt atggcactag    5820 tatttttatg aaatattatg ttaaaactgg gacaggggag aacctagggt gatattaacc   5880
aggggccatg aatcaccttt tggtctggag ggaagccttg gggctgatcg agttgttgcc   5940
cacagctgta tgattcccag ccagacacag cctcttagat gcagttctga agaagatggt   6000
accaccagtc tgactgtttc catcaagggt acactgcctt ctcaactcca aactgactct   6060
taagaagact gcattatatt tattactgta agaaaatatc acttgtcaat aaaatccata   6120
catttgtgt                                                          6129
```

<210> SEQ ID NO 2
<211> LENGTH: 1480
<212> TYPE: PRT
<213> ORGANISM: Homo sapiens

<400> SEQUENCE: 2

Met Gln Arg Ser Pro Leu Glu Lys Ala Ser Val Val Ser Lys Leu Phe

-continued

```
  1               5                  10                 15
Phe Ser Trp Thr Arg Pro Ile Leu Arg Lys Gly Tyr Arg Gln Arg Leu
            20                  25                  30

Glu Leu Ser Asp Ile Tyr Gln Ile Pro Ser Val Asp Ser Ala Asp Asn
            35                  40                  45

Leu Ser Glu Lys Leu Glu Arg Glu Trp Asp Arg Glu Leu Ala Ser Lys
 50                  55                  60

Lys Asn Pro Lys Leu Ile Asn Ala Leu Arg Arg Cys Phe Phe Trp Arg
 65                  70                  75                  80

Phe Met Phe Tyr Gly Ile Phe Leu Tyr Leu Gly Glu Val Thr Lys Ala
                 85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
            115                 120                 125

Leu Leu Phe Ile Val Arg Thr Leu Leu Leu His Pro Ala Ile Phe Gly
 130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                 165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
            195                 200                 205

Ala Leu Leu Met Gly Leu Ile Trp Glu Leu Leu Gln Ala Ser Ala Phe
 210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                 245                 250                 255

Glu Arg Leu Val Ile Thr Ser Glu Met Ile Glu Asn Ile Gln Ser Val
            260                 265                 270

Lys Ala Tyr Cys Trp Glu Glu Ala Met Glu Lys Met Ile Glu Asn Leu
            275                 280                 285

Arg Gln Thr Glu Leu Lys Leu Thr Arg Lys Ala Ala Tyr Val Arg Tyr
 290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                 325                 330                 335

Phe Thr Thr Ile Ser Phe Cys Ile Val Leu Arg Met Ala Val Thr Arg
            340                 345                 350

Gln Phe Pro Trp Ala Val Gln Thr Trp Tyr Asp Ser Leu Gly Ala Ile
            355                 360                 365

Asn Lys Ile Gln Asp Phe Leu Gln Lys Gln Glu Tyr Lys Thr Leu Glu
 370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                 405                 410                 415

Asn Asn Arg Lys Thr Ser Asn Gly Asp Asp Ser Leu Phe Phe Ser Asn
            420                 425                 430
```

```
Phe Ser Leu Leu Gly Thr Pro Val Leu Lys Asp Ile Asn Phe Lys Ile
            435                 440                 445

Glu Arg Gly Gln Leu Leu Ala Val Ala Gly Ser Thr Gly Ala Gly Lys
        450                 455                 460

Thr Ser Leu Leu Met Met Ile Met Gly Glu Leu Glu Pro Ser Glu Gly
465                 470                 475                 480

Lys Ile Lys His Ser Gly Arg Ile Ser Phe Cys Ser Gln Phe Ser Trp
                    485                 490                 495

Ile Met Pro Gly Thr Ile Lys Glu Asn Ile Ile Phe Gly Val Ser Tyr
                500                 505                 510

Asp Glu Tyr Arg Tyr Arg Ser Val Ile Lys Ala Cys Gln Leu Glu Glu
            515                 520                 525

Asp Ile Ser Lys Phe Ala Glu Lys Asp Asn Ile Val Leu Gly Glu Gly
        530                 535                 540

Gly Ile Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
                565                 570                 575

Tyr Leu Asp Val Leu Thr Glu Lys Glu Ile Phe Glu Ser Cys Val Cys
                580                 585                 590

Lys Leu Met Ala Asn Lys Thr Arg Ile Leu Val Thr Ser Lys Met Glu
            595                 600                 605

His Leu Lys Lys Ala Asp Lys Ile Leu Ile Leu Asn Glu Gly Ser Ser
        610                 615                 620

Tyr Phe Tyr Gly Thr Phe Ser Glu Leu Gln Asn Leu Gln Pro Asp Phe
625                 630                 635                 640

Ser Ser Lys Leu Met Gly Cys Asp Ser Phe Asp Gln Phe Ser Ala Glu
                645                 650                 655

Arg Arg Asn Ser Ile Leu Thr Glu Thr Leu His Arg Phe Ser Leu Glu
                660                 665                 670

Gly Asp Ala Pro Val Ser Trp Thr Glu Thr Lys Lys Gln Ser Phe Lys
            675                 680                 685

Gln Thr Gly Glu Phe Gly Glu Lys Arg Lys Asn Ser Ile Leu Asn Pro
        690                 695                 700

Ile Asn Ser Ile Arg Lys Phe Ser Ile Val Gln Lys Thr Pro Leu Gln
705                 710                 715                 720

Met Asn Gly Ile Glu Glu Asp Ser Asp Glu Pro Leu Glu Arg Arg Leu
                725                 730                 735

Ser Leu Val Pro Asp Ser Glu Gln Gly Glu Ala Ile Leu Pro Arg Ile
                740                 745                 750

Ser Val Ile Ser Thr Gly Pro Thr Leu Gln Ala Arg Arg Arg Gln Ser
            755                 760                 765

Val Leu Asn Leu Met Thr His Ser Val Asn Gln Gly Gln Asn Ile His
        770                 775                 780

Arg Lys Thr Thr Ala Ser Thr Arg Lys Val Ser Leu Ala Pro Gln Ala
785                 790                 795                 800

Asn Leu Thr Glu Leu Asp Ile Tyr Ser Arg Arg Leu Ser Gln Glu Thr
                805                 810                 815

Gly Leu Glu Ile Ser Glu Glu Ile Asn Glu Glu Asp Leu Lys Glu Cys
                820                 825                 830

Leu Phe Asp Asp Met Glu Ser Ile Pro Ala Val Thr Thr Trp Asn Thr
            835                 840                 845
```

```
Tyr Leu Arg Tyr Ile Thr Val His Lys Ser Leu Ile Phe Val Leu Ile
    850                 855                 860

Trp Cys Leu Val Ile Phe Leu Ala Glu Val Ala Ala Ser Leu Val Val
865                 870                 875                 880

Leu Trp Leu Leu Gly Asn Thr Pro Leu Gln Asp Lys Gly Asn Ser Thr
                885                 890                 895

His Ser Arg Asn Asn Ser Tyr Ala Val Ile Ile Thr Ser Thr Ser Ser
            900                 905                 910

Tyr Tyr Val Phe Tyr Ile Tyr Val Gly Val Ala Asp Thr Leu Leu Ala
            915                 920                 925

Met Gly Phe Phe Arg Gly Leu Pro Leu Val His Thr Leu Ile Thr Val
    930                 935                 940

Ser Lys Ile Leu His His Lys Met Leu His Ser Val Leu Gln Ala Pro
945                 950                 955                 960

Met Ser Thr Leu Asn Thr Leu Lys Ala Gly Gly Ile Leu Asn Arg Phe
                965                 970                 975

Ser Lys Asp Ile Ala Ile Leu Asp Asp Leu Leu Pro Leu Thr Ile Phe
            980                 985                 990

Asp Phe Ile Gln Leu Leu Leu Ile Val Ile Gly Ala Ile Ala Val Val
            995                 1000                1005

Ala Val Leu Gln Pro Tyr Ile Phe Val Ala Thr Val Pro Val Ile Val
    1010                1015                1020

Ala Phe Ile Met Leu Arg Ala Tyr Phe Leu Gln Thr Ser Gln Gln Leu
1025                1030                1035                1040

Lys Gln Leu Glu Ser Glu Gly Arg Ser Pro Ile Phe Thr His Leu Val
                1045                1050                1055

Thr Ser Leu Lys Gly Leu Trp Thr Leu Arg Ala Phe Gly Arg Gln Pro
            1060                1065                1070

Tyr Phe Glu Thr Leu Phe His Lys Ala Leu Asn Leu His Thr Ala Asn
            1075                1080                1085

Trp Phe Leu Tyr Leu Ser Thr Leu Arg Trp Phe Gln Met Arg Ile Glu
    1090                1095                1100

Met Ile Phe Val Ile Phe Phe Ile Ala Val Thr Phe Ile Ser Ile Leu
1105                1110                1115                1120

Thr Thr Gly Glu Gly Glu Gly Arg Val Gly Ile Ile Leu Thr Leu Ala
                1125                1130                1135

Met Asn Ile Met Ser Thr Leu Gln Trp Ala Val Asn Ser Ser Ile Asp
            1140                1145                1150

Val Asp Ser Leu Met Arg Ser Val Ser Arg Val Phe Lys Phe Ile Asp
            1155                1160                1165

Met Pro Thr Glu Gly Lys Pro Thr Lys Ser Thr Lys Pro Tyr Lys Asn
    1170                1175                1180

Gly Gln Leu Ser Lys Val Met Ile Ile Glu Asn Ser His Val Lys Lys
1185                1190                1195                1200

Asp Asp Ile Trp Pro Ser Gly Gly Gln Met Thr Val Lys Asp Leu Thr
                1205                1210                1215

Ala Lys Tyr Thr Glu Gly Gly Asn Ala Ile Leu Glu Asn Ile Ser Phe
            1220                1225                1230

Ser Ile Ser Pro Gly Gln Arg Val Gly Leu Leu Gly Arg Thr Gly Ser
            1235                1240                1245

Gly Lys Ser Thr Leu Leu Ser Ala Phe Leu Arg Leu Leu Asn Thr Glu
    1250                1255                1260

Gly Glu Ile Gln Ile Asp Gly Val Ser Trp Asp Ser Ile Thr Leu Gln
```

```
                1265                1270                1275                1280
        Gln Trp Arg Lys Ala Phe Gly Val Ile Pro Gln Lys Val Phe Ile Phe
                        1285                1290                1295
        Ser Gly Thr Phe Arg Lys Asn Leu Asp Pro Tyr Glu Gln Trp Ser Asp
                    1300                1305                1310
        Gln Glu Ile Trp Lys Val Ala Asp Glu Val Gly Leu Arg Ser Val Ile
                1315                1320                1325
        Glu Gln Phe Pro Gly Lys Leu Asp Phe Val Leu Val Asp Gly Gly Cys
            1330                1335                1340
        Val Leu Ser His Gly His Lys Gln Leu Met Cys Leu Ala Arg Ser Val
        1345                1350                1355                1360
        Leu Ser Lys Ala Lys Ile Leu Leu Leu Asp Glu Pro Ser Ala His Leu
                    1365                1370                1375
        Asp Pro Val Thr Tyr Gln Ile Ile Arg Arg Thr Leu Lys Gln Ala Phe
                1380                1385                1390
        Ala Asp Cys Thr Val Ile Leu Cys Glu His Arg Ile Glu Ala Met Leu
            1395                1400                1405
        Glu Cys Gln Gln Phe Leu Val Ile Glu Glu Asn Lys Val Arg Gln Tyr
            1410                1415                1420
        Asp Ser Ile Gln Lys Leu Leu Asn Glu Arg Ser Leu Phe Arg Gln Ala
        1425                1430                1435                1440
        Ile Ser Pro Ser Asp Arg Val Lys Leu Phe Pro His Arg Asn Ser Ser
                    1445                1450                1455
        Lys Cys Lys Ser Lys Pro Gln Ile Ala Ala Leu Lys Glu Glu Thr Glu
                1460                1465                1470
        Glu Glu Val Gln Asp Thr Arg Leu
                1475                1480

<210> SEQ ID NO 3
<211> LENGTH: 6126
<212> TYPE: DNA
<213> ORGANISM: Homo sapiens

<400> SEQUENCE: 3
aattggaagc aaatgacatc acagcaggtc agagaaaaag ggttgagcgg caggcaccca     60
gagtagtagg tctttggcat taggagcttg agcccagacg gccctagcag ggaccccagc    120
gcccgagaga ccatgcagag gtcgcctctg gaaaaggcca gcgttgtctc caaactttt     180
ttcagctgga ccagaccaat tttgaggaaa ggatacagac agcgcctgga attgtcagac    240
atataccaaa tcccttctgt tgattctgct gacaatctat ctgaaaaatt ggaaagagaa    300
tgggatagag agctggcttc aaagaaaaat cctaaactca ttaatgccct tcggcgatgt    360
tttttctgga gatttatgtt ctatggaatc ttttttatatt tagggaagt caccaaagca    420
gtacagcctc tcttactggg aagaatcata gcttcctatg acccggataa caaggaggaa    480
cgctctatcg cgatttatct aggcataggc ttatgccttc tctttattgt gaggacactg    540
ctcctacacc cagccatttt tggccttcat cacattggaa tgcagatgag aatagctatg    600
tttagtttga tttataagaa gactttaaag ctgtcaagcc gtgttctaga taaataagt    660
attggacaac ttgttagtct cctttccaac aacctgaaca aatttgatga aggacttgca    720
ttggcacatt tcgtgtggat cgctcctttg caagtggcac tcctcatggg gctaatctgg    780
gagttgttac aggcgtctgc cttctgtgga cttggtttcc tgatagtcct tgcccttttt    840
caggctgggc taggagaat gatgatgaag tacagagatc agagagctgg gaagatcagt    900
```

-continued

```
gaaagacttg tgattacctc agaaatgatt gaaaatatcc aatctgttaa ggcatactgc    960
tgggaagaag caatggaaaa aatgattgaa aacttaagac aaacagaact gaaactgact   1020
cggaaggcag cctatgtgag atacttcaat agctcagcct tcttcttctc agggttcttt   1080
gtggtgtttt tatctgtgct tccctatgca ctaatcaaag gaatcatcct ccggaaaata   1140
ttcaccacca tctcattctg cattgttctg cgcatggcgg tcactcggca atttccctgg   1200
gctgtacaaa catggtatga ctctcttgga gcaataaaca aaatacagga tttcttacaa   1260
aagcaagaat ataagacatt ggaatataac ttaacgacta cagaagtagt gatggagaat   1320
gtaacagcct tctgggagga gggatttggg gaattatttg agaaagcaaa acaaaacaat   1380
aacaatagaa aaacttctaa tggtgatgac agcctcttct tcagtaattt ctcacttctt   1440
ggtactcctg tcctgaaaga tattaatttc aagatagaaa gaggacagtt gttggcggtt   1500
gctggatcca ctggagcagg caagacttca cttctaatga tgattatggg agaactggag   1560
ccttcagagg gtaaaattaa gcacagtgga agaatttcat tctgttctca gttttcctgg   1620
attatgcctg gcaccattaa agaaaatatc atcggtgttt cctatgatga atatagatac   1680
agaagcgtca tcaaagcatg ccaactagaa gaggacatct ccaagtttgc agagaaagac   1740
aatatagttc ttggagaagg tggaatcaca ctgagtggag gtcaacgagc aagaatttct   1800
ttagcaagag cagtatacaa agatgctgat ttgtatttat tagactctcc ttttggatac   1860
ctagatgttt taacagaaaa agaaatattt gaaagctgtg tctgtaaact gatggctaac   1920
aaaactagga ttttggtcac ttctaaaatg gaacatttaa agaaagctga caaaatatta   1980
attttgaatg aaggtagcag ctattttat gggacatttt cagaactcca aaatctacag   2040
ccagacttta gctcaaaact catgggatgt gattctttcg accaatttag tgcagaaaga   2100
agaaattcaa tcctaactga daccttacac cgtttctcat tagaaggaga tgctcctgtc   2160
tcctggacag aaacaaaaaa acaatctttt aaacagactg agagtttgg ggaaaaaagg   2220 aagaattcta ttctcaatcc aatcaactct atacgaaaat tttccattgt gcaaaagact   2280
cccttacaaa tgaatggcat cgaagaggat tctgatgagc ctttagagag aaggctgtcc   2340
ttagtaccag attctgagca gggagaggcg atactgcctc gcatcagcgt gatcagcact   2400
ggccccacgc ttcaggcacg aaggaggcag tctgtcctga acctgatgac acactcagtt   2460
aaccaaggtc agaacattca ccgaaagaca acagcatcca cacgaaaagt gtcactggcc   2520
cctcaggcaa acttgactga actggatata tattcaagaa ggttatctca agaaactggc   2580
ttggaaataa gtgaagaaat taacgaagaa gacttaaagg agtgccttt tgatgatatg   2640 gagagcatac cagcagtgac tacatggaac acatacttc gatatattac tgtccacaag   2700
agcttaattt ttgtgctaat ttggtgctta gtaattttc tggcagaggt ggctgcttct   2760
ttggttgtgc tgtggctcct tggaaacact cctcttcaag acaaagggaa tagtactcat   2820
agtagaaata acagctatgc agtgattatc accagcacca gttcgtatta tgtgtttttac   2880 atttacgtgg gagtagccga cactttgctt gctatgggat tcttcagagg tctaccactg   2940
gtgcatactc taatcacagt gtcgaaaatt ttacaccaca aaatgttaca ttctgttctt   3000
caagcaccta tgtcaaccct caacacgttg aaagcaggtg ggattcttaa tagattctcc   3060
aaagatatag caattttgga tgaccttctg cctcttacca tatttgactt catccagttg   3120
ttattaattg tgattggagc tatagcagtt gtcgcagttt tacaaccta catctttgtt   3180 gcaacagtgc cagtgatagt ggcttttatt atgttgagag catatttcct ccaaacctca   3240
cagcaactca acaactgga atctgaaggc aggagtccaa ttttcactca tcttgttaca   3300
```

```
agcttaaaag gactatggac acttcgtgcc ttcggacggc agccttactt tgaaactctg    3360
ttccacaaag ctctgaattt acatactgcc aactggttct tgtacctgtc aacactgcgc    3420
tggttccaaa tgagaataga aatgattttt gtcatcttct tcattgctgt taccttcatt    3480 tccatttttaa caacaggaga aggagaagga agagttggta ttatcctgac tttagccatg    3540
aatatcatga gtacattgca gtgggctgta aactccagca tagatgtgga tagcttgatg    3600
cgatctgtga gccgagtctt taagttcatt gacatgccaa cagaaggtaa acctaccaag    3660
tcaaccaaac catacaagaa tggccaactc tcgaaagtta tgattattga gaattcacac    3720
gtgaagaaag atgacatctg gccctcaggg ggccaaatga ctgtcaaaga tctcacagca    3780
aaatacacag aaggtggaaa tgccatatta gagaacattt ccttctcaat aagtcctggc    3840
cagagggtgg gcctcttggg aagaactgga tcagggaaga gtactttgtt atcagctttt    3900
ttgagactac tgaacactga aggagaaatc cagatcgatg gtgtgtcttg ggattcaata    3960
actttgcaac agtggaggaa agcctttgga gtgataccac agaaagtatt tattttttct    4020
ggaacattta gaaaaaactt ggatccctat gaacagtgga gtgatcaaga aatatggaaa    4080
gttgcagatg aggttgggct cagatctgtg atagaacagt ttcctgggaa gcttgacttt    4140
gtccttgtgg atgggggctg tgtcctaagc catggccaca gcagttgat  gtgcttggct    4200 agatctgttc tcagtaaggc gaagatcttg ctgcttgatg aacccagtgc tcatttggat    4260
ccagtaacat accaaataat tagaagaact ctaaaacaag catttgctga ttgcacagta    4320
attctctgtg aacacaggat agaagcaatg ctggaatgcc aacaattttt ggtcatagaa    4380
gagaacaaag tgcggcagta cgattccatc cagaaactgc tgaacgagag gagcctcttc    4440
cggcaagcca tcagcccctc cgacagggtg aagctctttc cccaccggaa ctcaagcaag    4500
tgcaagtcta gccccagat tgctgctctg aagaggaga cagaagaaga ggtgcaagat    4560
acaaggcttt agagagcagc ataaatgttg acatgggaca tttgctcatg gaattggagc    4620
tcgtgggaca gtcacctcat ggaattggag ctcgtggaac agttacctct gcctcagaaa    4680
acaaggatga attaagtttt ttttttaaaaa agaaacattt ggtaagggga attgaggaca    4740
ctgtatgggg tcttgataaa tggcttcctg gcaatagtca aattgtgtga aaggtacttc    4800
aaatccttga agatttacca cttgtgtttt gcaagccaga ttttcctgaa aacccttgcc    4860
atgtgctagt aattggaaag gcagctctaa atgtcaatca gcctagttga tcagcttatt    4920
gtctagtgaa actcgttaat ttgtagtgtt ggagaagaac tgaaatcata cttcttaggg    4980
ttatgattaa gtaatgataa ctggaaactt cagcggttta tataagcttg tattcctttt    5040
tctctcctct ccccatgatg tttagaaaca caactatatt gtttgctaag cattccaact    5100
atctcatttc caagcaagta ttagaatacc acaggaacca caagactgca catcaaaata    5160
tgccccattc aacatctagt gagcagtcag gaaagagaac ttccagatcc tggaaatcag    5220
ggttagtatt gtccaggtct accaaaaatc tcaatatttc agataatcac aatacatccc    5280
ttacctggga aagggctgtt ataatctttc acagggggaca ggatggttcc cttgatgaag    5340
aagttgatat gccttttccc aactccagaa agtgacaagc tcacagacct tgaactaga    5400 gtttagctgg aaaagtatgt tagtgcaaat tgtcacagga cagcccttct ttccacagaa    5460
gctccaggta gagggtgtgt aagtagatag gccatgggca ctgtgggtag acacacatga    5520
agtccaagca tttagatgta taggttgatg gtggtatgtt ttcaggctag atgtatgtac    5580
ttcatgctgt ctacactaag agagaatgag agacacactg aagaagcacc aatcatgaat    5640
```

-continued

```
tagttttata tgcttctgtt ttataatttt gtgaagcaaa attttttctc taggaaatat    5700
ttattttaat aatgtttcaa acatatatta caatgctgta ttttaaaaga atgattatga    5760
attacatttg tataaaataa ttttttatatt tgaaatattg acttttttatg gcactagtat  5820 ttttatgaaa tattatgtta aaactgggac aggggagaac ctagggtgat attaaccagg    5880
ggccatgaat cacctttggg tctggaggga agccttgggg ctgatcgagt tgttgcccac    5940
agctgtatga ttcccagcca gacacagcct cttagatgca gttctgaaga agatggtacc    6000
accagtctga ctgtttccat caagggtaca ctgccttctc aactccaaac tgactcttaa    6060
gaagactgca ttatatttat tactgtaaga aaatatcact tgtcaataaa atccatacat    6120
ttgtgt                                                               6126
```

<210> SEQ ID NO 4
<211> LENGTH: 1479
<212> TYPE: PRT
<213> ORGANISM: Homo sapiens

<400> SEQUENCE: 4

```
Met Gln Arg Ser Pro Leu Glu Lys Ala Ser Val Val Ser Lys Leu Phe
  1               5                  10                  15

Phe Ser Trp Thr Arg Pro Ile Leu Arg Lys Gly Tyr Arg Gln Arg Leu
                 20                  25                  30

Glu Leu Ser Asp Ile Tyr Gln Ile Pro Ser Val Asp Ser Ala Asp Asn
             35                  40                  45

Leu Ser Glu Lys Leu Glu Arg Glu Trp Asp Arg Glu Leu Ala Ser Lys
         50                  55                  60

Lys Asn Pro Lys Leu Ile Asn Ala Leu Arg Arg Cys Phe Phe Trp Arg
     65                  70                  75                  80

Phe Met Phe Tyr Gly Ile Phe Leu Tyr Leu Gly Glu Val Thr Lys Ala
                 85                  90                  95

Val Gln Pro Leu Leu Leu Gly Arg Ile Ile Ala Ser Tyr Asp Pro Asp
                100                 105                 110

Asn Lys Glu Glu Arg Ser Ile Ala Ile Tyr Leu Gly Ile Gly Leu Cys
            115                 120                 125

Leu Leu Phe Ile Val Arg Thr Leu Leu Leu His Pro Ala Ile Phe Gly
        130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
        195                 200                 205

Ala Leu Leu Met Gly Leu Ile Trp Glu Leu Leu Gln Ala Ser Ala Phe
    210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
            260                 265                 270

Lys Ala Tyr Cys Trp Glu Glu Ala Met Glu Lys Met Ile Glu Asn Leu
        275                 280                 285
```

-continued

```
Arg Gln Thr Glu Leu Lys Leu Thr Arg Lys Ala Ala Tyr Val Arg Tyr
    290                 295                 300
Phe Asn Ser Ser Ala Phe Phe Ser Gly Phe Phe Val Val Phe Leu
305                 310                 315                 320
Ser Val Leu Pro Tyr Ala Leu Ile Lys Gly Ile Ile Leu Arg Lys Ile
                325                 330                 335
Phe Thr Thr Ile Ser Phe Cys Ile Val Leu Arg Met Ala Val Thr Arg
                340                 345                 350
Gln Phe Pro Trp Ala Val Gln Thr Trp Tyr Asp Ser Leu Gly Ala Ile
            355                 360                 365
Asn Lys Ile Gln Asp Phe Leu Gln Lys Gln Glu Tyr Lys Thr Leu Glu
370                 375                 380
Tyr Asn Leu Thr Thr Thr Glu Val Val Met Glu Asn Val Thr Ala Phe
385                 390                 395                 400
Trp Glu Glu Gly Phe Gly Glu Leu Phe Glu Lys Ala Lys Gln Asn Asn
                405                 410                 415
Asn Asn Arg Lys Thr Ser Asn Gly Asp Asp Ser Leu Phe Phe Ser Asn
                420                 425                 430
Phe Ser Leu Leu Gly Thr Pro Val Leu Lys Asp Ile Asn Phe Lys Ile
            435                 440                 445
Glu Arg Gly Gln Leu Leu Ala Val Ala Gly Ser Thr Gly Ala Gly Lys
450                 455                 460
Thr Ser Leu Leu Met Met Ile Met Gly Glu Leu Glu Pro Ser Glu Gly
465                 470                 475                 480
Lys Ile Lys His Ser Gly Arg Ile Ser Phe Cys Ser Gln Phe Ser Trp
                485                 490                 495
Ile Met Pro Gly Thr Ile Lys Glu Asn Ile Ile Gly Val Ser Tyr Asp
            500                 505                 510
Glu Tyr Arg Tyr Arg Ser Val Ile Lys Ala Cys Gln Leu Glu Glu Asp
            515                 520                 525
Ile Ser Lys Phe Ala Glu Lys Asp Asn Ile Val Leu Gly Glu Gly Gly
530                 535                 540
Ile Thr Leu Ser Gly Gly Gln Arg Ala Arg Ile Ser Leu Ala Arg Ala
545                 550                 555                 560
Val Tyr Lys Asp Ala Asp Leu Tyr Leu Leu Asp Ser Pro Phe Gly Tyr
                565                 570                 575
Leu Asp Val Leu Thr Glu Lys Glu Ile Phe Glu Ser Cys Val Cys Lys
            580                 585                 590
Leu Met Ala Asn Lys Thr Arg Ile Leu Val Thr Ser Lys Met Glu His
            595                 600                 605
Leu Lys Lys Ala Asp Lys Ile Leu Ile Leu Asn Glu Gly Ser Ser Tyr
610                 615                 620
Phe Tyr Gly Thr Phe Ser Glu Leu Gln Asn Leu Gln Pro Asp Phe Ser
625                 630                 635                 640
Ser Lys Leu Met Gly Cys Asp Ser Phe Asp Gln Phe Ser Ala Glu Arg
                645                 650                 655
Arg Asn Ser Ile Leu Thr Glu Thr Leu His Arg Phe Ser Leu Glu Gly
                660                 665                 670
Asp Ala Pro Val Ser Trp Thr Glu Thr Lys Lys Gln Ser Phe Lys Gln
            675                 680                 685
Thr Gly Glu Phe Gly Glu Lys Arg Lys Asn Ser Ile Leu Asn Pro Ile
690                 695                 700
```

-continued

```
Asn Ser Ile Arg Lys Phe Ser Ile Val Gln Lys Thr Pro Leu Gln Met
705                 710                 715                 720

Asn Gly Ile Glu Glu Asp Ser Asp Glu Pro Leu Glu Arg Arg Leu Ser
            725                 730                 735

Leu Val Pro Asp Ser Glu Gln Gly Glu Ala Ile Leu Pro Arg Ile Ser
        740                 745                 750

Val Ile Ser Thr Gly Pro Thr Leu Gln Ala Arg Arg Gln Ser Val
    755                 760                 765

Leu Asn Leu Met Thr His Ser Val Asn Gln Gly Gln Asn Ile His Arg
770                 775                 780

Lys Thr Thr Ala Ser Thr Arg Lys Val Ser Leu Ala Pro Gln Ala Asn
785                 790                 795                 800

Leu Thr Glu Leu Asp Ile Tyr Ser Arg Arg Leu Ser Gln Glu Thr Gly
                805                 810                 815

Leu Glu Ile Ser Glu Glu Ile Asn Glu Glu Asp Leu Lys Glu Cys Leu
            820                 825                 830

Phe Asp Asp Met Glu Ser Ile Pro Ala Val Thr Thr Trp Asn Thr Tyr
        835                 840                 845

Leu Arg Tyr Ile Thr Val His Lys Ser Leu Ile Phe Val Leu Ile Trp
    850                 855                 860

Cys Leu Val Ile Phe Leu Ala Glu Val Ala Ala Ser Leu Val Val Leu
865                 870                 875                 880

Trp Leu Leu Gly Asn Thr Pro Leu Gln Asp Lys Gly Asn Ser Thr His
                885                 890                 895

Ser Arg Asn Asn Ser Tyr Ala Val Ile Ile Thr Ser Thr Ser Ser Tyr
            900                 905                 910

Tyr Val Phe Tyr Ile Tyr Val Gly Val Ala Asp Thr Leu Leu Ala Met
        915                 920                 925

Gly Phe Phe Arg Gly Leu Pro Leu Val His Thr Leu Ile Thr Val Ser
    930                 935                 940

Lys Ile Leu His His Lys Met Leu His Ser Val Leu Gln Ala Pro Met
945                 950                 955                 960

Ser Thr Leu Asn Thr Leu Lys Ala Gly Gly Ile Leu Asn Arg Phe Ser
                965                 970                 975

Lys Asp Ile Ala Ile Leu Asp Asp Leu Leu Pro Leu Thr Ile Phe Asp
            980                 985                 990

Phe Ile Gln Leu Leu Leu Ile Val Ile Gly Ala Ile Ala Val Val Ala
        995                 1000                1005

Val Leu Gln Pro Tyr Ile Phe Val Ala Thr Val Pro Val Ile Val Ala
    1010                1015                1020

Phe Ile Met Leu Arg Ala Tyr Phe Leu Gln Thr Ser Gln Gln Leu Lys
1025                1030                1035                1040

Gln Leu Glu Ser Glu Gly Arg Ser Pro Ile Phe Thr His Leu Val Thr
                1045                1050                1055

Ser Leu Lys Gly Leu Trp Thr Leu Arg Ala Phe Gly Arg Gln Pro Tyr
            1060                1065                1070

Phe Glu Thr Leu Phe His Lys Ala Leu Asn Leu His Thr Ala Asn Trp
        1075                1080                1085

Phe Leu Tyr Leu Ser Thr Leu Arg Trp Phe Gln Met Arg Ile Glu Met
    1090                1095                1100

Ile Phe Val Ile Phe Phe Ile Ala Val Thr Phe Ile Ser Ile Leu Thr
1105                1110                1115                1120

Thr Gly Glu Gly Glu Gly Arg Val Gly Ile Ile Leu Thr Leu Ala Met
```

Asn Ile Met Ser Thr Leu Gln Trp Ala Val Asn Ser Ser Ile Asp Val
              1140                1145                1150

Asp Ser Leu Met Arg Ser Val Ser Arg Val Phe Lys Phe Ile Asp Met
        1155                1160                1165

Pro Thr Glu Gly Lys Pro Thr Lys Ser Thr Lys Pro Tyr Lys Asn Gly
    1170                1175                1180

Gln Leu Ser Lys Val Met Ile Glu Asn Ser His Val Lys Lys Asp
1185                1190                1195                1200

Asp Ile Trp Pro Ser Gly Gly Gln Met Thr Val Lys Asp Leu Thr Ala
          1205                1210                1215

Lys Tyr Thr Glu Gly Gly Asn Ala Ile Leu Glu Asn Ile Ser Phe Ser
        1220                1225                1230

Ile Ser Pro Gly Gln Arg Val Gly Leu Leu Gly Arg Thr Gly Ser Gly
      1235                1240                1245

Lys Ser Thr Leu Leu Ser Ala Phe Leu Arg Leu Leu Asn Thr Glu Gly
    1250                1255                1260

Glu Ile Gln Ile Asp Gly Val Ser Trp Asp Ser Ile Thr Leu Gln Gln
1265                1270                1275                1280

Trp Arg Lys Ala Phe Gly Val Ile Pro Gln Lys Val Phe Ile Phe Ser
          1285                1290                1295

Gly Thr Phe Arg Lys Asn Leu Asp Pro Tyr Glu Gln Trp Ser Asp Gln
        1300                1305                1310

Glu Ile Trp Lys Val Ala Asp Glu Val Gly Leu Arg Ser Val Ile Glu
      1315                1320                1325

Gln Phe Pro Gly Lys Leu Asp Phe Val Leu Val Asp Gly Gly Cys Val
    1330                1335                1340

Leu Ser His Gly His Lys Gln Leu Met Cys Leu Ala Arg Ser Val Leu
1345                1350                1355                1360

Ser Lys Ala Lys Ile Leu Leu Leu Asp Glu Pro Ser Ala His Leu Asp
          1365                1370                1375

Pro Val Thr Tyr Gln Ile Ile Arg Arg Thr Leu Lys Gln Ala Phe Ala
        1380                1385                1390

Asp Cys Thr Val Ile Leu Cys Glu His Arg Ile Glu Ala Met Leu Glu
      1395                1400                1405

Cys Gln Gln Phe Leu Val Ile Glu Glu Asn Lys Val Arg Gln Tyr Asp
    1410                1415                1420

Ser Ile Gln Lys Leu Leu Asn Glu Arg Ser Leu Phe Arg Gln Ala Ile
1425                1430                1435                1440

Ser Pro Ser Asp Arg Val Lys Leu Phe Pro His Arg Asn Ser Ser Lys
          1445                1450                1455

Cys Lys Ser Lys Pro Gln Ile Ala Ala Leu Lys Glu Glu Thr Glu Glu
        1460                1465                1470

Glu Val Gln Asp Thr Arg Leu
      1475

<210> SEQ ID NO 5
<211> LENGTH: 6129
<212> TYPE: DNA
<213> ORGANISM: Homo sapiens

<400> SEQUENCE: 5
aattggaagc aaatgacatc acagcaggtc agagaaaaag ggttgagcgg caggcaccca    60
gagtagtagg tctttggcat taggagcttg agcccagacg gccctagcag ggaccccagc   120

```
gcccgagaga ccatgcagag gtcgcctctg gaaaaggcca gcgttgtctc caaactttt      180
ttcagctgga ccagaccaat tttgaggaaa ggatacagac agcgcctgga attgtcagac      240
atataccaaa tcccttctgt tgattctgct gacaatctat ctgaaaaatt ggaaagagaa      300
tgggatagag agctggcttc aaagaaaaat cctaaactca ttaatgccct tcggcgatgt      360
ttttctgga gatttatgtt ctatggaatc tttttatatt taggggaagt caccaaagca       420
gtacagcctc tcttactggg aagaatcata gcttcctatg acccggataa caaggaggaa      480
cgctctatcg cgatttatct aggcataggc ttatgccttc tctttattgt gaggacactg      540
ctcctacacc cagccatttt tggccttcat cacattggaa tgcagatgag aatagctatg      600
tttagtttga tttataagaa gactttaaag ctgtcaagcc gtgttctaga taaataagt       660
attggacaac ttgttagtct cctttccaac aacctgaaca aatttgatga aggacttgca      720
ttggcacatt tcgtgtggat cgctcctttg caagtggcac tcctcatggg gctaatctgg      780
gagttgttac aggcgtctgc cttctgtgga cttggtttcc tgatagtcct tgcccttttt      840
caggctgggc tagggagaat gatgatgaag tacagagatc agagagctgg gaagatcagt      900
gaaagacttg tgattacctc agaaatgatt gaaaatatcc aatctgttaa ggcatactgc      960
tgggaagaag caatggaaaa aatgattgaa aacttaagac aaacagaact gaaactgact     1020
cggaaggcag cctatgtgag atacttcaat agctcagcct tcttcttctc agggttcttt     1080
gtggtgtttt tatctgtgct tccctatgca ctaatcaaag aatcatcct ccggaaaata      1140
ttcaccacca tctcattctg cattgttctg cgcatggcgg tcactcggca atttccctgg     1200
gctgtacaaa catggtatga ctctcttgga gcaataaaca aaatacagga tttcttacaa     1260
aagcaagaat ataagacatt ggaatataac ttaacgacta cagaagtagt gatggagaat     1320
gtaacagcct tctgggagga gggatttggg gaattatttg agaaagcaaa acaaaacaat     1380
aacaatagaa aaacttctaa tggtgatgac agcctcttct tcagtaattt ctcacttctt     1440
ggtactcctg tcctgaaaga tattaatttc aagatagaaa gaggacagtt gttggcggtt     1500
gctggatcca ctggagcagg caagacttca cttctaatga tgattatggg agaactggag     1560
ccttcagagg gtaaaattaa gcacagtgga agaatttcat tctgttctca gttttcctgg     1620
attatgcctg gcaccattaa agaaaatatc atctttggtg tttcctatga tgaatataga     1680
tacagaagcg tcatcaaagc atgccaacta gaagaggaca tctccaagtt tgcagagaaa     1740
gacaatatag ttcttggaga aggtggaatc acactgagtg gagaycaacg agcaagaatt     1800
tctttagcaa gagcagtata caaagatgct gatttgtatt tattagactc tccttttgga     1860
tacctagatg ttttaacaga aaaagaaata tttgaaagct gtgtctgtaa actgatggct     1920
aacaaaacta ggattttggt cacttctaaa atggaacatt taaagaaagc tgacaaaata     1980
ttaattttga atgaaggtag cagctatttt tatgggacat tttcagaact ccaaaatcta     2040
cagccagact ttagctcaaa actcatggga tgtgattctt cgaccaatt tagtgcagaa       2100
agaagaaatt caatcctaac tgagaccta caccgtttct cattagaagg atgctcct         2160
gtctcctgga cagaaacaaa aaaacaatct tttaaacaga ctggagagtt tggggaaaaa     2220
aggaagaatt ctattctcaa tccaatcaac tctatacgaa aattttccat tgtgcaaaag     2280
actcccttac aaatgaatgg catcgaagag gattctgatg agcctttaga gagaaggctg     2340
tccttagtac cagattctga gcagggagag gcgatactgc ctcgcatcag cgtgatcagc     2400
actggcccca cgcttcaggc acgaaggagg cagtctgtcc tgaacctgat gacacactca     2460
```

-continued

```
gttaaccaag gtcagaacat tcaccgaaag acaacagcat ccacacgaaa agtgtcactg    2520 gccccctcagg caaacttgac tgaactggat atatattcaa gaaggttatc tcaagaaact    2580
ggcttggaaa taagtgaaga aattaacgaa gaagacttaa aggagtgcct ttttgatgat    2640
atggagagca taccagcagt gactacatgg aacacatacc ttcgatatat tactgtccac    2700
aagagcttaa tttttgtgct aatttggtgc ttagtaattt ttctggcaga ggtggctgct    2760
tctttggttg tgctgtggct ccttggaaac actcctcttc aagacaaagg aatagtact    2820 catagtagaa ataacagcta tgcagtgatt atcaccagca ccagttcgta ttatgtgttt    2880
tacatttacg tgggagtagc cgacactttg cttgctatgg gattcttcag aggtctacca    2940
ctggtgcata ctctaatcac agtgtcgaaa attttacacc acaaaatgtt acattctgtt    3000
cttcaagcac ctatgtcaac cctcaacacg ttgaaagcag gtgggattct taatagattc    3060
tccaaagata tagcaatttt ggatgacctt ctgcctctta ccatatttga cttcatccag    3120
ttgttattaa ttgtgattgg agctatagca gttgtcgcag ttttacaacc ctacatctt    3180 gttgcaacag tgccagtgat agtggctttt attatgttga gagcatattt cctccaaacc    3240
tcacagcaac tcaaacaact ggaatctgaa ggcaggagtc caattttcac tcatcttgtt    3300
acaagcttaa aaggactatg gacacttcgt gccttcggac ggcagcctta ctttgaaact    3360
ctgttccaca aagctctgaa tttacatact gccaactggt tcttgtacct gtcaacactg    3420
cgctggttcc aaatgagaat agaaatgatt tttgtcatct tcttcattgc tgttaccttc    3480
atttccattt taacaacagg agaaggagaa ggaagagttg gtattatcct gactttagcc    3540
atgaatatca tgagtacatt gcagtgggct gtaaactcca gcatagatgt ggatagcttg    3600
atgcgatctg tgagccgagt cttttaagttc attgacatgc caacagaagg taaacctacc    3660
aagtcaacca aaccatacaa gaatggccaa ctctcgaaag ttatgattat tgagaattca    3720
cacgtgaaga aagatgacat ctggccctca gggggccaaa tgactgtcaa agatctcaca    3780
gcaaaataca cagaaggtgg aaatgccata ttagagaaca tttccttctc aataagtcct    3840
ggccagaggg tgggcctctt gggaagaact ggatcaggga gagtactttt gttatcagct    3900 ttttttgagac tactgaacac tgaaggagaa atccagatcg atggtgtgtc ttgggattca    3960
ataactttgc aacagtggag gaaagccttt ggagtgatac cacagaaagt atttattttt    4020
tctggaacat ttagaaaaaa cttggatccc tatgaacagt ggagtgatca agaaatatgg    4080
aaagttgcag atgaggttgg gctcagatct gtgatagaac agtttcctgg gaagcttgac    4140
tttgtccttg tggatggggg ctgtgtccta agccatggcc acaagcagtt gatgtgcttg    4200
gctagatctg ttctcagtaa ggcgaagatc ttgctgcttg atgaacccag tgctcatttg    4260
gatccagtaa cataccaaat aattagaaga actctaaaac aagcatttgc tgattgcaca    4320
gtaattctct gtgaacacag gatagaagca atgctgaat gccaacaatt tttggtcata    4380
gaagagaaca aagtgcggca gtacgattcc atccagaaac tgctgaacga gaggagcctc    4440
ttccggcaag ccatcagccc ctccgacagg gtgaagctct tccccaccg gaactcaagc    4500 aagtgcaagt ctaagcccca gattgctgct ctgaaagagg acagaagaga gaggtgcaa    4560 gatacaaggc tttagagagc agcataaatg ttgacatggg acatttgctc atggaattgg    4620
agctcgtggg acagtcacct catggaattg gagctcgtgg aacagttacc tctgcctcag    4680
aaaacaagga tgaattaagt tttttttaa aaagaaaca tttggtaagg ggaattgagg    4740
acactgatat gggtcttgat aaatggcttc ctggcaatag tcaaattgtg tgaaaggtac    4800
ttcaaatcct tgaagattta ccacttgtgt tttgcaagcc agattttcct gaaaacccttt    4860
```

```
gccatgtgct agtaattgga aaggcagctc taaatgtcaa tcagcctagt tgatcagctt    4920
attgtctagt gaaactcgtt aatttgtagt gttggagaag aactgaaatc atacttctta    4980
gggttatgat taagtaatga taactggaaa cttcagcggt ttatataagc ttgtattcct    5040
ttttctctcc tctccccatg atgtttagaa acacaactat attgtttgct aagcattcca    5100
actatctcat ttccaagcaa gtattagaat accacaggaa ccacaagact gcacatcaaa    5160
atatgcccca ttcaacatct agtgagcagt caggaaagag aacttccaga tcctggaaat    5220
cagggttagt attgtccagg tctaccaaaa atctcaatat ttcagataat cacaatacat    5280
cccttacctg ggaaagggct gttataatct ttcacagggg acaggatggt tcccttgatg    5340
aagaagttga tatgcctttt cccaactcca gaaagtgaca agctcacaga cctttgaact    5400
agagtttagc tggaaaagta tgttagtgca aattgtcaca ggacagccct tctttccaca    5460
gaagctccag gtagagggtg tgtaagtaga taggccatgg gcactgtggg tagacacaca    5520
tgaagtccaa gcatttagat gtataggttg atggtggtat gttttcaggc tagatgtatg    5580
tacttcatgc tgtctacact aagagagaat gagagacaca ctgaagaagc accaatcatg    5640
aattagtttt atatgcttct gttttataat tttgtgaagc aaaattttt  ctctaggaaa    5700
tatttatttt aataatgttt caaacatata ttacaatgct gtattttaaa agaatgatta    5760
tgaattacat ttgtataaaa taattttat  atttgaaata ttgactttt  atggcactag    5820
tattttatg  aaatattatg ttaaaactgg gacaggggag aacctagggt gatattaacc    5880
aggggccatg aatcaccttt tggtctggag ggaagccttg gggctgatcg agttgttgcc    5940
cacagctgta tgattcccag ccagacacag cctcttagat gcagttctga agaagatggt    6000
accaccagtc tgactgtttc catcaagggt acactgcctt ctcaactcca aactgactct    6060
taagaagact gcattatatt tattactgta agaaaatatc acttgtcaat aaaatccata    6120
catttgtgt                                                            6129
```

<210> SEQ ID NO 6
<211> LENGTH: 1480
<212> TYPE: PRT
<213> ORGANISM: Homo sapiens

<400> SEQUENCE: 6

```
Met Gln Arg Ser Pro Leu Glu Lys Ala Ser Val Val Ser Lys Leu Phe
 1               5                  10                  15

Phe Ser Trp Thr Arg Pro Ile Leu Arg Lys Gly Tyr Arg Gln Arg Leu
                20                  25                  30

Glu Leu Ser Asp Ile Tyr Gln Ile Pro Ser Val Asp Ser Ala Asp Asn
            35                  40                  45

Leu Ser Glu Lys Leu Glu Arg Glu Trp Asp Arg Glu Leu Ala Ser Lys
        50                  55                  60

Lys Asn Pro Lys Leu Ile Asn Ala Leu Arg Arg Cys Phe Phe Trp Arg
    65                  70                  75                  80

Phe Met Phe Tyr Gly Ile Phe Leu Tyr Leu Gly Glu Val Thr Lys Ala
                85                  90                  95

Val Gln Pro Leu Leu Leu Gly Arg Ile Ile Ala Ser Tyr Asp Pro Asp
               100                 105                 110

Asn Lys Glu Glu Arg Ser Ile Ala Ile Tyr Leu Gly Ile Gly Leu Cys
           115                 120                 125

Leu Leu Phe Ile Val Arg Thr Leu Leu Leu His Pro Ala Ile Phe Gly
       130                 135                 140
```

```
Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
                180                 185                 190

Glu Gly Leu Ala Leu Ala His Phe Val Trp Ile Ala Pro Leu Gln Val
            195                 200                 205

Ala Leu Leu Met Gly Leu Ile Trp Glu Leu Leu Gln Ala Ser Ala Phe
210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
                260                 265                 270

Lys Ala Tyr Cys Trp Glu Glu Ala Met Glu Lys Met Ile Glu Asn Leu
                275                 280                 285

Arg Gln Thr Glu Leu Lys Leu Thr Arg Lys Ala Ala Tyr Val Arg Tyr
290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
                340                 345                 350

Gln Phe Pro Trp Ala Val Gln Thr Trp Tyr Asp Ser Leu Gly Ala Ile
                355                 360                 365

Asn Lys Ile Gln Asp Phe Leu Gln Lys Gln Glu Tyr Lys Thr Leu Glu
                370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
                420                 425                 430

Phe Ser Leu Leu Gly Thr Pro Val Leu Lys Asp Ile Asn Phe Lys Ile
                435                 440                 445

Glu Arg Gly Gln Leu Leu Ala Val Ala Gly Ser Thr Gly Ala Gly Lys
450                 455                 460

Thr Ser Leu Leu Met Met Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr
                500                 505                 510

Asp Glu Tyr Arg Tyr Arg Ser Val Ile Lys Ala Cys Gln Leu Glu Glu
                515                 520                 525

Asp Ile Ser Lys Phe Ala Glu Lys Asp Asn Ile Val Leu Gly Glu Gly
                530                 535                 540

Gly Ile Thr Leu Ser Gly Asp Gln Arg Ala Arg Ile Ser Leu Ala Arg
545                 550                 555                 560
```

-continued

```
Ala Val Tyr Lys Asp Ala Asp Leu Tyr Leu Leu Asp Ser Pro Phe Gly
            565                 570                 575

Tyr Leu Asp Val Leu Thr Glu Lys Glu Ile Phe Glu Ser Cys Val Cys
            580                 585                 590

Lys Leu Met Ala Asn Lys Thr Arg Ile Leu Val Thr Ser Lys Met Glu
            595                 600                 605

His Leu Lys Lys Ala Asp Lys Ile Leu Ile Leu Asn Glu Gly Ser Ser
            610                 615                 620

Tyr Phe Tyr Gly Thr Phe Ser Glu Leu Gln Asn Leu Gln Pro Asp Phe
625                 630                 635                 640

Ser Ser Lys Leu Met Gly Cys Asp Ser Phe Asp Gln Phe Ser Ala Glu
            645                 650                 655

Arg Arg Asn Ser Ile Leu Thr Glu Thr Leu His Arg Phe Ser Leu Glu
            660                 665                 670

Gly Asp Ala Pro Val Ser Trp Thr Glu Thr Lys Lys Gln Ser Phe Lys
            675                 680                 685

Gln Thr Gly Glu Phe Gly Glu Lys Arg Lys Asn Ser Ile Leu Asn Pro
            690                 695                 700

Ile Asn Ser Ile Arg Lys Phe Ser Ile Val Gln Lys Thr Pro Leu Gln
705                 710                 715                 720

Met Asn Gly Ile Glu Glu Asp Ser Asp Glu Pro Leu Glu Arg Arg Leu
            725                 730                 735

Ser Leu Val Pro Asp Ser Glu Gln Gly Glu Ala Ile Leu Pro Arg Ile
            740                 745                 750

Ser Val Ile Ser Thr Gly Pro Thr Leu Gln Ala Arg Arg Arg Gln Ser
            755                 760                 765

Val Leu Asn Leu Met Thr His Ser Val Asn Gln Gly Gln Asn Ile His
            770                 775                 780

Arg Lys Thr Thr Ala Ser Thr Arg Lys Val Ser Leu Ala Pro Gln Ala
785                 790                 795                 800

Asn Leu Thr Glu Leu Asp Ile Tyr Ser Arg Arg Leu Ser Gln Glu Thr
            805                 810                 815

Gly Leu Glu Ile Ser Glu Glu Ile Asn Glu Glu Asp Leu Lys Glu Cys
            820                 825                 830

Leu Phe Asp Asp Met Glu Ser Ile Pro Ala Val Thr Thr Trp Asn Thr
            835                 840                 845

Tyr Leu Arg Tyr Ile Thr Val His Lys Ser Leu Ile Phe Val Leu Ile
            850                 855                 860

Trp Cys Leu Val Ile Phe Leu Ala Glu Val Ala Ala Ser Leu Val Val
865                 870                 875                 880

Leu Trp Leu Leu Gly Asn Thr Pro Leu Gln Asp Lys Gly Asn Ser Thr
            885                 890                 895

His Ser Arg Asn Asn Ser Tyr Ala Val Ile Ile Thr Ser Thr Ser Ser
            900                 905                 910

Tyr Tyr Val Phe Tyr Ile Tyr Val Gly Val Ala Asp Thr Leu Leu Ala
            915                 920                 925

Met Gly Phe Phe Arg Gly Leu Pro Leu Val His Thr Leu Ile Thr Val
            930                 935                 940

Ser Lys Ile Leu His His Lys Met Leu His Ser Val Leu Gln Ala Pro
945                 950                 955                 960

Met Ser Thr Leu Asn Thr Leu Lys Ala Gly Gly Ile Leu Asn Arg Phe
            965                 970                 975

Ser Lys Asp Ile Ala Ile Leu Asp Asp Leu Leu Pro Leu Thr Ile Phe
```

-continued

```
                980              985              990
Asp Phe Ile Gln Leu Leu Ile Val Ile Gly Ala Ile Ala Val Val
            995             1000             1005
Ala Val Leu Gln Pro Tyr Ile Phe Val Ala Thr Val Pro Val Ile Val
1010             1015             1020
Ala Phe Ile Met Leu Arg Ala Tyr Phe Leu Gln Thr Ser Gln Leu
1025             1030             1035             1040
Lys Gln Leu Glu Ser Glu Gly Arg Ser Pro Ile Phe Thr His Leu Val
            1045             1050             1055
Thr Ser Leu Lys Gly Leu Trp Thr Leu Arg Ala Phe Gly Arg Gln Pro
            1060             1065             1070
Tyr Phe Glu Thr Leu Phe His Lys Ala Leu Asn Leu His Thr Ala Asn
            1075             1080             1085
Trp Phe Leu Tyr Leu Ser Thr Leu Arg Trp Phe Gln Met Arg Ile Glu
            1090             1095             1100
Met Ile Phe Val Ile Phe Phe Ile Ala Val Thr Phe Ile Ser Ile Leu
1105             1110             1115             1120
Thr Thr Gly Glu Gly Glu Gly Arg Val Gly Ile Ile Leu Thr Leu Ala
            1125             1130             1135
Met Asn Ile Met Ser Thr Leu Gln Trp Ala Val Asn Ser Ser Ile Asp
            1140             1145             1150
Val Asp Ser Leu Met Arg Ser Val Ser Arg Val Phe Lys Phe Ile Asp
            1155             1160             1165
Met Pro Thr Glu Gly Lys Pro Thr Lys Ser Thr Lys Pro Tyr Lys Asn
            1170             1175             1180
Gly Gln Leu Ser Lys Val Met Ile Ile Glu Asn Ser His Val Lys Lys
1185             1190             1195             1200
Asp Asp Ile Trp Pro Ser Gly Gly Gln Met Thr Val Lys Asp Leu Thr
            1205             1210             1215
Ala Lys Tyr Thr Glu Gly Gly Asn Ala Ile Leu Glu Asn Ile Ser Phe
            1220             1225             1230
Ser Ile Ser Pro Gly Gln Arg Val Gly Leu Leu Gly Arg Thr Gly Ser
            1235             1240             1245
Gly Lys Ser Thr Leu Leu Ser Ala Phe Leu Arg Leu Leu Asn Thr Glu
            1250             1255             1260
Gly Glu Ile Gln Ile Asp Gly Val Ser Trp Asp Ser Ile Thr Leu Gln
1265             1270             1275             1280
Gln Trp Arg Lys Ala Phe Gly Val Ile Pro Gln Lys Val Phe Ile Phe
            1285             1290             1295
Ser Gly Thr Phe Arg Lys Asn Leu Asp Pro Tyr Glu Gln Trp Ser Asp
            1300             1305             1310
Gln Glu Ile Trp Lys Val Ala Asp Glu Val Gly Leu Arg Ser Val Ile
            1315             1320             1325
Glu Gln Phe Pro Gly Lys Leu Asp Phe Val Leu Val Asp Gly Gly Cys
            1330             1335             1340
Val Leu Ser His Gly His Lys Gln Leu Met Cys Leu Ala Arg Ser Val
1345             1350             1355             1360
Leu Ser Lys Ala Lys Ile Leu Leu Leu Asp Glu Pro Ser Ala His Leu
            1365             1370             1375
Asp Pro Val Thr Tyr Gln Ile Ile Arg Arg Thr Leu Lys Gln Ala Phe
            1380             1385             1390
Ala Asp Cys Thr Val Ile Leu Cys Glu His Arg Ile Glu Ala Met Leu
            1395             1400             1405
```

```
Glu Cys Gln Gln Phe Leu Val Ile Glu Glu Asn Lys Val Arg Gln Tyr
    1410                1415                1420

Asp Ser Ile Gln Lys Leu Leu Asn Glu Arg Ser Leu Phe Arg Gln Ala
1425             1430                1435                1440

Ile Ser Pro Ser Asp Arg Val Lys Leu Phe Pro His Arg Asn Ser Ser
                1445                1450                1455

Lys Cys Lys Ser Lys Pro Gln Ile Ala Ala Leu Lys Glu Glu Thr Glu
            1460                1465                1470

Glu Glu Val Gln Asp Thr Arg Leu
        1475                1480
```

COMPOSITIONS AND METHODS FOR CYSTIC FIBROSIS THERAPY

CROSS-REFERENCE TO RELATED APPLICATION

This application is a continuation-in-part of U.S. Ser. No. 08/951,912, filed Oct. 16, 1997.

TECHNICAL FIELD

The present invention relates generally to the treatment of cystic fibrosis. The invention is more particularly related to compositions comprising one or more compounds such as flavones and/or isoflavones, which may be used to activate chloride transport (i.e., absorption and/or secretion) in epithelial tissues of the airways, the intestine, the pancreas and other exocrine glands, and for cystic fibrosis therapy.

BACKGROUND OF THE INVENTION

Cystic fibrosis is a lethal genetic disease afflicting approximately 30,000 individuals in the United States. Approximately 1 in 2500 Caucasians is born with the disease, making it the most common lethal, recessively inherited disease in that population.

Cystic fibrosis affects the secretory epithelia of a variety of tissues, altering the transport of water, salt and other solutes into and out of the blood stream. In particular, the ability of epithelial cells in the airways, pancreas and other tissues to transport chloride ions, and accompanying sodium and water, is severely reduced in cystic fibrosis patients, resulting in respiratory, pancreatic and intestinal ailments. The principle clinical manifestation of cystic fibrosis is the resulting respiratory disease, characterized by airway obstruction due to the presence of a thick mucus that is difficult to clear from airway surfaces. This thickened airway liquid contributes to recurrent bacterial infections and progressively impaired respiration, eventually resulting in death.

In cystic fibrosis, defective chloride transport is generally due to a mutation in a chloride channel known as the cystic fibrosis transmembrane conductance regulator (CFTR; see Riordan et al., *Science* 245:1066–73, 1989). CFTR is a linear chloride channel found in the plasma membrane of certain epithelial cells, where it regulates the flow of chloride ions in response to phosphorylation by a cyclic AMP-dependent kinase. Many mutations of CFTR have been reported, the most common of which is a deletion of phenylalanine at position 508 (ΔF508-CFTR), which is present in approximately 70% of patients with cystic fibrosis. A glycine to aspartate substitution at position 551 (G551D-CFTR) occurs in approximately 1% of cystic fibrosis patients.

Current treatments for cystic fibrosis generally focus on controlling infection through antibiotic therapy and promoting mucus clearance by use of postural drainage and chest percussion. However, even with such treatments, frequent hospitalization is often required as the disease progresses. New therapies designed to increase chloride ion conductance in airway epithelial cells have been proposed, but their long term beneficial effects have not been established and such therapies are not presently available to patients.

Accordingly, improvements are needed in the treatment of cystic fibrosis. The present invention fulfills this need and further provides other related advantages.

SUMMARY OF THE INVENTION

Briefly stated, the present invention provides compositions and methods for enhancing chloride transport in epithelial cells and for the therapy of cystic fibrosis. Within one aspect, the present invention provides methods for enhancing chloride transport in epithelial cells, comprising contacting epithelial cells with a compound selected from the group consisting of flavones and isoflavones, wherein the compound is capable of stimulating chloride transport and wherein the compound is not genistein. Within certain embodiments, the compound is (a) a polyphenolic compound having the general formula:

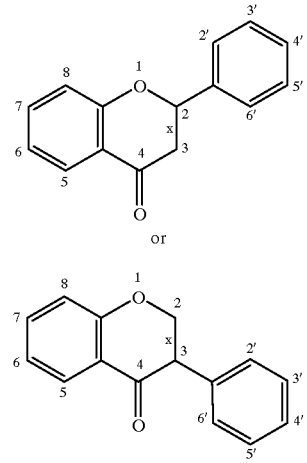

wherein carbon atoms at positions 2, 3, 5, 6, 7, 8, 2', 3', 4', 5' and 6' are bonded to a moiety independently selected from the group consisting of hydrogen atoms, hydroxyl groups and methoxyl groups, and wherein X is a single bond or a double bond; or (b) a stereoisomer or glycoside derivative of any of the foregoing polyphenolic compounds. Such compounds include, within certain embodiments, quercetin, apigenin, kaempferol, biochanin A, flavanone, flavone, dihydroxyflavone, trimethoxy-apigenin, apigenin 7-O-neohesperidoside, fisetin, rutin, daidzein and prunetin. For enhancing chloride transport in airway epithelial cells of a mammal, compounds may be administered orally or by inhalation. Other epithelial cells that may be employed include intestinal, pancreas, gallbladder, sweat duct, salivary gland and mammary epithelial cells. Within certain embodiments, the compound is combined with a substance that increases expression of a CFTR; and/or a chemical chaperone that increases trafficking of a CFTR to the plasma membrane.

Within other aspects, methods for enhancing chloride transport in epithelial cells may comprise contacting epithelial cells with a compound selected from the group consisting of reservatrol, ascorbic acid, ascorbate salts and dehydroascorbic acid. Such compounds may further be used in combination with a flavone or isoflavone as provided above.

Within other aspects, the present invention provides methods for treating cystic fibrosis in a patient, comprising administering to a patient a compound as described above, wherein the compound is capable of stimulating chloride transport. Within certain embodiments, the compound is genistein, quercetin, apigenin, kaempferol, biochanin A, flavanone, flavone, dihydroxyflavone, trimethoxy-apigenin, apigenin 7-O-neohesperidoside, fisetin, rutin, daidzein or prunetin. Within other embodiments, the compound is reservatrol, ascorbic acid, ascorbate salts and dehydroascorbic acid. Such compounds may be administered alone or in combination. Compounds may be administered orally or by inhalation. Within certain embodiments, the compound is combined with a substance that increases expression of a CFTR; and/or a chemical chaperone that increases trafficking of a CFTR to the plasma membrane.

Within further related aspects, the present invention provides methods for increasing chloride ion conductance in airway epithelial cells of a patient afflicted with cystic fibrosis, wherein the patient's CFTR protein has a deletion at position 508, the method comprising administering to a mammal one or more compounds as described above, wherein the compound is capable of stimulating chloride secretion in the airway epithelial cells.

Within still further related aspects, the present invention provides methods for increasing chloride ion conductance in airway epithelial cells of a patient afflicted with cystic fibrosis, wherein the patient's CFTR protein has a mutation at position 551, the method comprising administering to a mammal one or more compounds as described above, wherein the compound is capable of stimulating chloride secretion in the airway epithelial cells.

Within further aspects, pharmaceutical compositions for treatment of cystic fibrosis are provided, comprising (a) one or more flavones or isoflavones capable of stimulating chloride transport and (b) one or more of: (i) a compound that increases expression of a CFTR in an epithelial cell; and/or (ii) a chemical chaperone that increases trafficking of a CFTR to a plasma membrane in an epithelial cell; and; and in combination with a pharmaceutically acceptable carrier. Within certain embodiments, the flavone or isoflavone may be genistein, quercetin, apigenin, kaempferol, biochanin A, flavanone, flavone, dihydroxyflavone, trimethoxy-apigenin, apigenin 7-O-neohesperidoside, fisetin, rutin, daidzein and/or prunetin, in combination with a pharmaceutically acceptable carrier.

Within still further aspects, a pharmaceutical composition for treatment of cystic fibrosis may comprise: (a) a polyphenolic compound having the general formula:

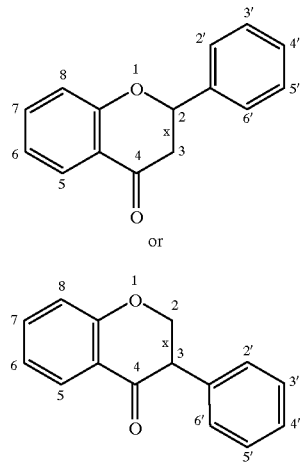

wherein carbon atoms at positions 2, 3, 5, 6, 7, 8, 2', 3', 4', 5' and 6' are bonded to a moiety independently selected from the group consisting of hydrogen atoms, hydroxyl groups and methoxyl groups, and wherein X is a single bond or a double bond; or a stereoisomer or glycoside derivative of any of the foregoing polyphenolic compounds; (b) a compound selected from the group consisting of reservatrol, ascorbic acid, ascorbate salts and dehydroascorbic acid; and (c) a physiologically acceptable carrier.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 12A shows a recording from a patient with the genotype G551D/ΔF508. Amiloride, chloride free solution and isoproterenol were added as indicated. The addition of genistein, as indicated, hyperpolarized nasal PD. FIG. 12B is a graph illustrating the average responses of nasal PD to genistein and quercetin of four CF patients with the G551D mutation. The filled bars show, for comparison, the respective responses in healthy subjects.

FIG. 13A is a graph showing the stimulation of transepithelial chloride currents by reservatrol (100 µM), flavanone (100 µM), flavone (200 µM), apigenin (20 µM), apigenin 7-O-neohesperidoside (30 µM), kaempferol (20 µM), fisetin (100 µM), quercetin (30 µM), rutin (30 µM), genistein (30 µM), daidzein (50 µM), biochanin A (100 µM) and prunetin (100 µM) in Calu-3 monolayers. Experiments were performed in the presence of 10 µM forskolin. Stimulated currents are plotted relative to forskolin stimulated increase (forskolin stimulated currents are 100%). FIG. 13B is a recording showing the effect of 7,4'-Dihydroxyflavone on chloride current in unstimulated tissue. This recording shows a dose-dependent stimulation of transepithelial short-circuit current (Isc) across Calu-3 monolayers by 7,4'-Dihydroxyflavone. Increasing concentrations of 7,4'-Dihydroxyflavone (as indicated in µM) were added to mucosal side and dose-dependently stimulated chloride currents. Currents were recorded with a serosal-to-mucosal chloride gradient at 0 mV and pulses were obtained at 2 mV. FIG. 13C is a recording illustrating the effect of trimethoxy-apigenin. This recording shows dose-dependent stimulation of transepithelial short-circuit current (Isc) across Calu-3 monolayers by trimethoxy-apigenin. Increasing concentrations of trimethoxy-apigenin (as indicated in µM) were added to mucosal side and dose-dependently stimulated chloride currents. Experiment was performed on unstimulated tissue. Currents were recorded with a serosal-to-mucosal chloride gradient at 0 mV and pulses were obtained at 2 mV.

DETAILED DESCRIPTION OF THE INVENTION

Figure 1:
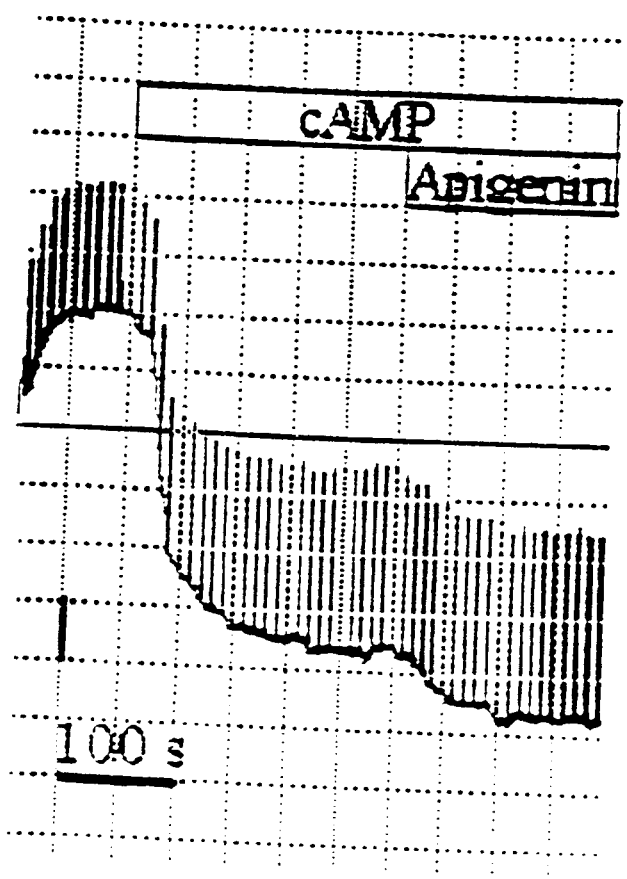
FIG. 1 is a recording of transepithelial short-circuit current (Y axis) as a function of time (X axis), showing the effect of apigenin on the current across a Calu-3 cell monolayer. Measurements were performed in an Ussing chamber, where the basolateral membrane was permeabilized with α-toxin and a chloride gradient was applied across the apical membrane as a driving force. Tissue was first stimulated with cAMP (100 μM). Apigenin (50 μM) was subsequently added as indicated. The horizontal bar represents 100 seconds, and the vertical bar represents 12 $\mu A/cm^2$.

As noted above, the present invention is generally directed to compositions and methods for the treatment of diseases characterized by defective chloride transport in epithelial tissues, including cystic fibrosis, and diseases with excessive accumulation of mucus, including cystic fibrosis, chronic bronchitis and asthma. It has been found, within the context of the present invention, that certain flavones and isoflavones, as well as other polyphenolic compounds, are capable of stimulating CFTR-mediated chloride transport in epithelial tissues (e.g., tissues of the airways, intestine, pancreas and other exocrine glands) in a cyclic-AMP independent manner. Ascorbic acid and derivatives thereof may also, or alternatively, be used within such methods. It has further been found, within the context of the present invention, that such compounds stimulate chloride transport in cells with a mutated CFTR (e.g., ΔF508-CFTR or G551D-CFTR). Such therapeutic compounds may be administered to patients afflicted with cystic fibrosis as described herein.

The term "flavones," as used herein refers to a compound based on the core structure of flavone:

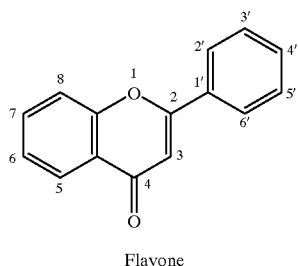

Flavone

An "isoflavone" is an isomer of a flavone (i.e., the phenyl moiety at position 2 is moved to position 3), and having the core structure shown below:

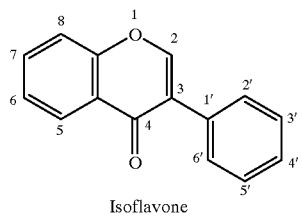

Isoflavone

Certain flavones and isoflavones have the structure:

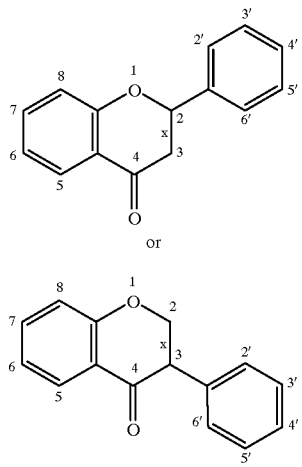

or wherein carbon atoms at positions 2, 3, 5, 6, 7, 8, 2', 3', 4', 5' and 6' are bonded to a moiety independently selected from the group consisting of hydrogen atoms, hydroxyl groups and methoxyl groups, and wherein X is a single bond or a double bond. Stereoisomers and glycoside derivatives of such polyphenolic compounds may also be used within the methods provided herein.

Many flavones are naturally-occurring compounds, but synthetic flavones and isoflavones are also encompassed by the present invention. A flavone or isoflavone may be modified to comprise any of a variety of functional groups, such as hydroxyl and/or ether groups. Preferred flavones comprise one or more hydroxyl groups, such as the trihydroxyflavone apigenin, the tetrahydroxyflavone kaempferol and the pentahydroxyflavone quercetin. Preferred isoflavones comprise one or more hydroxyl and/or methoxy groups, such as the methoxy, dihydroxy isoflavone biochanin A. Genistein is yet another preferred isoflavone for use within the methods provided herein.

Flavones and isoflavones for use within the context of the present invention have the ability to stimulate chloride transport in epithelial tissues. Such transport may result in secretion or absorption of chloride ions. The ability to stimulate chloride transport may be assessed using any of a variety of systems. For example, in vitro assays using a mammalian trachea or a cell line, such as the permanent airway cell line Calu-3 (ATCC Accession Number HTB55) may be employed. Alternatively, the ability to stimulate chloride transport may be evaluated within an in vivo assay employing a mammalian nasal epithelium. In general, the ability to stimulate chloride transport may be assessed by evaluating CFTR-mediated currents across a membrane by employing standard Ussing chamber (see Ussing and Zehrahn, *Acta. Physiol. Scand.* 23:110–127, 1951) or nasal potential difference measurements (see Knowles et al., *Hum. Gene Therapy* 6:445–455, 1995). Within such assays, a flavone or isoflavone that stimulates a statistically significant increase in chloride transport at a concentration of about 1–300 μM is said to stimulate chloride transport.

Within one in vitro assay, the level of chloride transport may be evaluated using mammalian pulmonary cell lines, such as Calu-3 cells, or primary bovine tracheal cultures. In general, such assays employ cell monolayers, which may be prepared by standard cell culture techniques. Within such systems, CFTR-mediated chloride current may be monitored in an Ussing chamber using intact epithelia. Alternatively, chloride transport may be evaluated using epithelial tissue in which the basolateral membrane is permeabilized with *Staphylococcus aureus* α-toxin, and in which a chloride gradient is imposed across the apical membrane (see Illek et al., *Am. J. Physiol.* 270:C265–75, 1996). In either system, chloride transport is evaluated in the presence and absence of a test compound (i.e., a flavone or isoflavone), and those compounds that stimulate chloride transport as described above may be used within the methods provided herein.

Within another in vitro assay for evaluating chloride transport, cells are transfected with a chloride channel gene (e.g., CFTR) having a mutation associated with cystic fibrosis. Any CFTR gene that is altered relative to the normal human sequence provided in SEQ ID NO: 1, such that the encoded protein contains a mutation associated with cystic fibrosis, may be employed within such an assay. The most common disease-causing mutation in cystic fibrosis is a deletion of phenylalanine at position 508 in the CFTR protein (ΔF508-CFTR; SEQ ID NO:4). Accordingly, the use of a CFTR gene encoding ΔF508-CFTR is preferred. However, genes encoding other altered CFTR proteins (e.g., G551D-CFTR; containing a glycine to aspartate point mutation at position 551; SEQ ID NO:6) may also be used. Cells such as NIH 3T3 fibroblasts may be transfected with an altered CTFR gene, such as ΔF508-CFTR, using well known techniques (see Anderson et al., *Science* 25:679–682, 1991). The effect of a compound on chloride transport in such cells may be evaluated by monitoring CFTR-mediated currents using the patch clamp method (see Hamill et al., *Pflugers Arch.* 391:85–100, 1981) with and without compound application.

Within another in vitro assay, a mutant CFTR may be microinjected into cells such as Xenopus oocytes. Chloride conductance mediated by the CFTR mutant in the presence and absence of a test compound may be monitored with the two electrode voltage clamp method (see Miledi et al., *Proc. R. Soc. Lond. Biol.* 218:481–484, 1983).

Alternatively, such assays may be performed using a mammalian trachea, such as a primary cow tracheal epithelium using the Ussing chamber technique as described above. Such assays are performed in the presence and absence of test compound to identify flavone and isoflavones that stimulate chloride transport.

Any of the above assays may be performed following pretreatment of the cells with a substance that increases the concentration of CFTR mutants in the plasma membrane. Such substances include chemical chaperones, which support correct trafficking of the mutant CFTR to the membrane, and compounds that increase expression of CFTR in the cell (e.g., transcriptional activators). A "chemical chaperone," as used herein is any molecule that increases trafficking of proteins to a cell membrane. More specifically, a chemical chaperone within the context of the present invention increases trafficking of a mutant CFTR (e.g., the Δ508-CFTR and/or G551D-CFTR) to the membrane by a statistically significant amount. Chemical chaperones for use herein include, but are not limited to, glycerol, dimethylsulfoxide, trimethylamine N-oxide, taurin, methylamine and deoxyspergualin (see Brown et al., *Cell Stress Chaperones* 1:117–125, 1996; Jiang et al., *Amer. J. Physiol.-Cell Physiol.* 44:C171–C178, 1998). Compounds that increase expression of CFTR in the cell include 4-phenylbutyrate (Rubenstein et al., *J. Clin. Invest.* 100:2457–2465, 1997) and sodium butyrate (Cheng et al., *Am. J. Physiol.* 268:L615–624, 1995). Other compounds that increase the level of CFTR in the plasma membrane (by increasing correct trafficking and/or expression of the CFTR) may be readily identified using well known techniques, such as immunohistochemical techniques, to evaluate effects on levels of plasma membrane CFTR.

In vivo, chloride secretion may be assessed using measurements of nasal potential differences in a mammal, such as a human or a mouse. Such measurements may be performed on the inferior surface of the inferior turbinate following treatment of the mucosal surface with a test compound during perfusion with the sodium transport blocker amiloride in chloride-free solution. The nasal potential difference is measured as the electrical potential measured on the nasal mucosa with respect to a skin electrode placed on a slightly scratched skin part (see Alton et al., *Eur. Respir. J.* 3:922–926, 1990) or with respect to a subcutaneous needle (see Knowles et al., *Hum. Gene Therapy* 6:445–455, 1995). Nasal potential difference is evaluated in the presence and absence of test compound, and those compounds that results in a statistically significant increase in nasal potential difference stimulate chloride transport.

Compounds as provided herein may generally be used to chloride transport within any of a variety of CFTR-expressing epithelial cells. CFTR is expressed in may epithelial cells, including intestinal, airway, pancreas, gallbladder, sweat duct, salivary gland and mammary epithelia. All such CFTR-expressing organs are subject to stimulation my the compounds provided herein.

As noted above, any flavone or isoflavone that stimulates chloride transport within at least one of the above assays may be used for therapy of cystic fibrosis, other diseases characterized by abnormally high mucus accumulation in the airways or intestinal disorders such as constipation. Preferred therapeutic compounds include flavones and isoflavones that occur naturally in plants and are part of the human diet. Preferred compounds include genistein (4',5,7-trihydroxyisoflavone), as well as quercetin (3,3',4',5,7-pentahydroxyflavone), apigenin (4'5,7-trihydroxyflavone), kaempferol (3,4',5,7-tetrahydroxyflavone) and biochanin A (4'-methoxy-5,7-dihydroxyisoflavone), as depicted below:

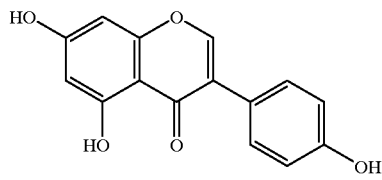

Genistein

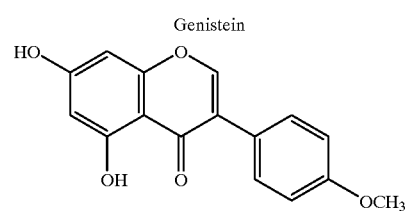

Biochanin A

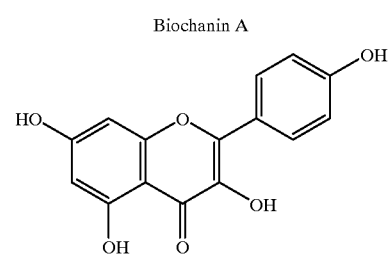

Kaempferol

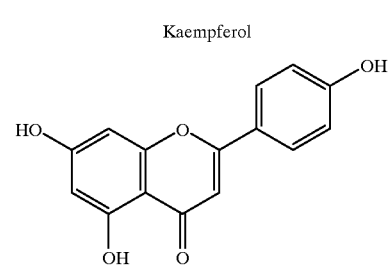

Apigenin

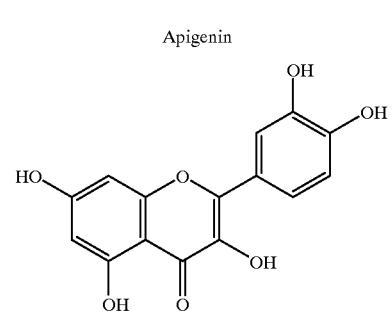

Quercetin

Other suitable therapeutic compounds may be identified using the resentative assays as described herein. Additional representative flavones and flavones include flavanone, flavone, dihydroxyflavone, trimethoxy-apigenin, genin 7-O-neohesperidoside, fisetin, rutin, daidzein and prunetin. Representative vones and isoflavones are summarized in TableI and II. s

TABLE I

Flavonoids

| No. | Name | X | C3 | C5 | C7 | C3' | C4' |
|---|---|---|---|---|---|---|---|
| 1 | Apigenin | = | | OH | OH | | OH |
| 2 | Apigenin7-O-neohesperidoside | = | | OH | ONeo | | OH |
| 3 | Dihydroxyflavone | = | | OH | | | OH |
| 4 | Flavone | = | | | | | |
| 5 | Flavanone | — | | | | | |
| 6 | Fisetin | = | OH | | OH | OH | OH |
| 7 | Kaempferol | = | OH | OH | OH | | OH |
| 8 | Quercetin | = | OH | OH | OH | OH | OH |
| 9 | Rutin | = | ORut | | OH | OH | OH |
| 10 | Trimethoxy-apigenin | = | H | OCH3 | OCH3 | | OCH3 | where = a double bond,
— is a single bond,
ONeo is Neohesperidoside,
ORut is rutinoside,
OCH3 is methoxy,
OH is hydroxy

TABLE II

Isoflavonoids

| No. | Name | X | C5 | C7 | C4' |
|---|---|---|---|---|---|
| 11 | Biochanin | = | OH | OH | OCH3 |
| 12 | Daidzein | = | | OH | OH |
| 13 | Genistein | = | OH | OH | OH |
| 14 | Prunetin | = | OH | OCH3 | OH | where = a double bond, — is a single bond, ONeo is Neohesperidoside, ORut is rutinoside, OCH3 is methoxy, OH is hydroxy.

Genistein, quercetin, apigenin, kaempferol, biochanin A and other flavones and isoflavones may generally be prepared using well known techniques, such as those described by Shakhova et al., *Zh. Obshch. Khim.* 32:390, 1962; Farooq et al., *Arch. Pharm.* 292:792, 1959; and Ichikawa et al., *Org. Prep. Prog. Int.* 14:183, 1981. Alternatively, such compounds may be commercially available (e.g, from Indofine Chemical Co., Inc., Somerville, N.J. or Sigma-Aldrich, St. Louis, Mo.). Further modifications to such compounds may be made using conventional organic chemistry techniques, which are well known to those of ordinary skill in the art.

As noted above, other polyphenolic compounds may be used within the methods provided herein. For example, trihydroxystilbenes such as reservatrol (trans-3,5,4'-trihydroxystilbene) may be employed. Reservatrol is a polyphenolic compound having the following structure:

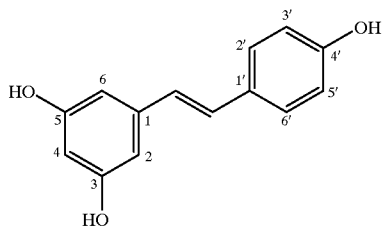

Other compounds that may be used within the methods provided herein are ascorbic acid and derivatives thereof. Such compounds include L-ascorbic acid (L-xyloascorbic acid), dehydrascorbic acid (L-thero-2,3-Hexodiulosoinic acid γ-lactone) and salts foregoing acids.

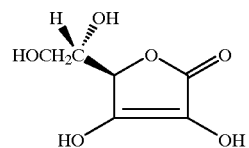

L-Ascorbic Acid

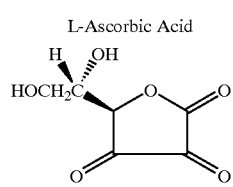

Dehydroascorbic Acid

Within certain preferred embodiments, ascorbic acid or a derivative thereof is used in combination with a polyphenolic compound as described above. Certain representative combinations include ascorbic acid and one or more flavenoids and/or isoflavenoids (such as genistein and ascorbic acid; and kaempferol and ascorbic acid). Ascorbic acid may generally be used to treat or prevent genetic loss of chloride secretory function (e.g. cystic fibrosis), as well as other related loss or reduced chloride secretory function (e.g., intestinal constipation, dry eye syndrome and obstructive airway diseases).

For in vivo use, a therapeutic compound as described herein is generally incorporated into a pharmaceutical composition prior to administration. Within such compositions, one or more therapeutic compounds as described herein are present as active ingredient(s) (i.e., are present at levels sufficient to provide a statistically significant effect on nasal potential difference, as measured using a representative assay as provided herein). A pharmaceutical composition comprises one or more such compounds in combination with any physiologically acceptable carrier(s) and/or excipient(s) known to those skilled in the art to be suitable for the particular mode of administration. In addition, other pharmaceutically active ingredients (including other therapeutic agents) may, but need not, be present within the composition.

Within certain methods provided herein, a flavone or isoflavone may be combined with a substance that increases the concentration of CFTR mutants in the plasma membrane of a cell. As noted above, such substances include chemical chaperones, which support correct trafficking of the mutant CFTR to the membrane, and compounds that increase expression of CFTR in the membrane. These substances may be contained within the same pharmaceutical composition or may be administered separately. Preferred chemical chaperones include glycerol, dimethylsulfoxide, trimethylamine N-oxide, taurin, methylamine and deoxyspergualin, and compounds that increase expression of CFTR in the membrane include 4-phenylbutyrate and sodium butyrate. The use of flavenoid and/or isoflavenoid compounds, as described herein, in combination with such substances may increase mutant CFTR activity, and ameliorate symptoms of cystic fibrosis.

Administration may be achieved by a variety of different routes. One preferred route is oral administration of a composition such as a pill, capsule or suspension. Such compositions may be prepared according to any method known in the art, and may comprise any of a variety of inactive ingredients. Suitable excipients for use within such compositions include inert diluents (which may be solid materials, aqueous solutions and/or oils) such as calcium or sodium carbonate, lactose, calcium or sodium phosphate, water, arachis oil, peanut oil liquid paraffin or olive oil; granulating and disintegrating agents such as maize starch, gelatin or acacia and/or lubricating agents such as magnesium stearate, stearic acid or talc. Other inactive ingredients that may, but need not, be present include one or more suspending agents (e.g., sodium carboxymethylcellulose, methylcellulose, hydroxypropylmethylcellulose, sodium alginate, polyvinylpyrrolidone, gum tragacanth and gum acacia), thickeners (e.g., beeswax, paraffin or cetyl alcohol), dispersing or wetting agents, preservatives (e.g., antioxidants such as ascorbic acid), coloring agents, sweetening agents and/or flavoring agents.

A pharmaceutical composition may be prepared with carriers that protect active ingredients against rapid elimination from the body, such as time release formulations or coatings. Such carriers include controlled release formulations, such as, but not limited to, microencapsulated delivery systems, and biodegradable, biocompatible polymers, such as ethylene vinyl acetate, polyanhydrides, polyglycolic acid, polyorthoesters, polylactic acid and others known to those of ordinary skill in the art.

Particularly preferred are methods in which the therapeutic compound(s) are directly administered as a pressurized aerosol or nebulized formulation to the patient's lungs via inhalation. Such formulations may contain any of a variety of known aerosol propellants useful for endopulmonary and/or intranasal inhalation administration. In addition, water may be present, with or without any of a variety of cosolvents, surfactants, stabilizers (e.g., antioxidants, chelating agents, inert gases and buffers). For compositions to be administered from multiple dose containers, antimicrobial agents are typically added. Such compositions are also generally filtered and sterilized, and may be lyophilized to provide enhanced stability and to improve solubility.

Pharmaceutical compositions are administered in an amount, and with a frequency, that is effective to inhibit or alleviate the symptoms of cystic fibrosis and/or to delay the progression of the disease. The effect of a treatment may be clinically determined by nasal potential difference measurements as described herein. The precise dosage and duration of treatment may be determined empirically using known testing protocols or by testing the compositions in model systems known in the art and extrapolating therefrom. Dosages may also vary with the severity of the disease. A pharmaceutical composition is generally formulated and administered to exert a therapeutically useful effect while minimizing undesirable side effects. In general, an oral dose ranges from about 200 mg to about 1000 mg, which may be administered 1 to 3 times per day. Compositions administered as an aerosol are generally designed to provide a final concentration of about 10 to 50 $\mu$M at the airway surface, and may be administered 1 to 3 times per day. It will be apparent that, for any particular subject, specific dosage regimens may be adjusted over time according to the individual need.

As noted above, a pharmaceutical composition may be administered to a mammal to stimulate chloride transport, and to treat cystic fibrosis. Patients that may benefit from administration of a therapeutic compound as described herein are those afflicted with cystic fibrosis. Such patients may be identified based on standard criteria that are well known in the art, including the presence of abnormally high salt concentrations in the sweat test, the presence of high nasal potentials, or the presence of a cystic fibrosis-associated mutation. Activation of chloride transport may also be beneficial in other diseases that show abnormally high mucus accumulation in the airways, such as asthma and chronic bronchitis. Similarly, intestinal constipation may benefit from activation of chloride transport by a flavone or isoflavone as provided herein.

SUMMARY OF SEQUENCE LISTING

SEQ ID NO:1 is a DNA sequence encoding human CFTR.
SEQ ID NO:2 is an amino acid sequence of human CFTR.
SEQ ID NO:3 is a DNA sequence encoding human CFTR with the $\Delta$F508 mutation.
SEQ ID NO:4 is an amino acid sequence of human CFTR with the $\Delta$F508 mutation.
SEQ ID NO:5 is a DNA sequence encoding human CFTR with the G551D mutation.
SEQ ID NO:6 is an amino acid sequence of human CFTR with the G551D mutation.

The following Examples are offered by way of illustration and not by way of limitation.

EXAMPLES

Example 1

Stimulation of Chloride Transport by Representative Flavones and Isoflavones in Airway Cells This Example illustrates the use of the representative compounds apigenin, quercetin and biochanin A to enhance chloride secretion in Calu-3 human pulmonary cultures or in primary bovine tracheal cultures.

A Calu-3 cell monolayer was prepared in an Ussing chamber as described by Illek et al., *Am. J. Physiol.* 270:C265–275, 1996. The basolateral membrane was permeabilized with $\alpha$-toxin and a chloride gradient was applied across the apical membrane as a driving force (see Illek et al, *Am. J. Physiol.* 270:C265–C275, 1996). The tissue was first stimulated with cAMP (100 $\mu$M), and then with a representative flavone or isoflavone.

Figure 2:
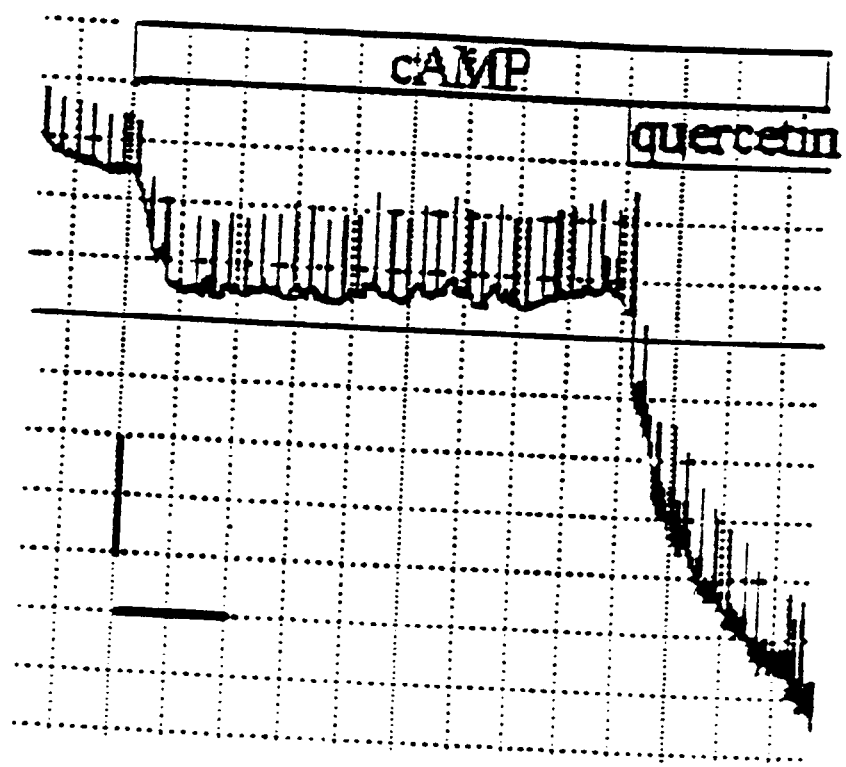
FIG. 2 is a recording showing the effect of quercetin on transepithelial short-circuit current across a Calu-3 cell monolayer in an Ussing chamber, where the basolateral membrane was permeabilized with α-toxin and a chloride gradient was applied across the apical membrane as a driving force. Tissue was first stimulated with cAMP (100 μM). Quercetin (30 μM) was subsequently added as indicated. Bars are 140 seconds (horizontal) and 12 $\mu A/cm^2$ (vertical).

As shown in FIGS. 1 and 2, subsequent addition of apigenin or quercetin further stimulated chloride current. FIG. 1 illustrates the short circuit current across the Calu-3 cell monolayer before and after addition of apigenin (50 $\mu$M). FIG. 2 illustrates the effect of quercetin (30 $\mu$M) on chloride current across a Calu-3 monolayer. In both cases, the flavone stimulated chloride current beyond the stimulation achieved by cAMP.

Figure 3:
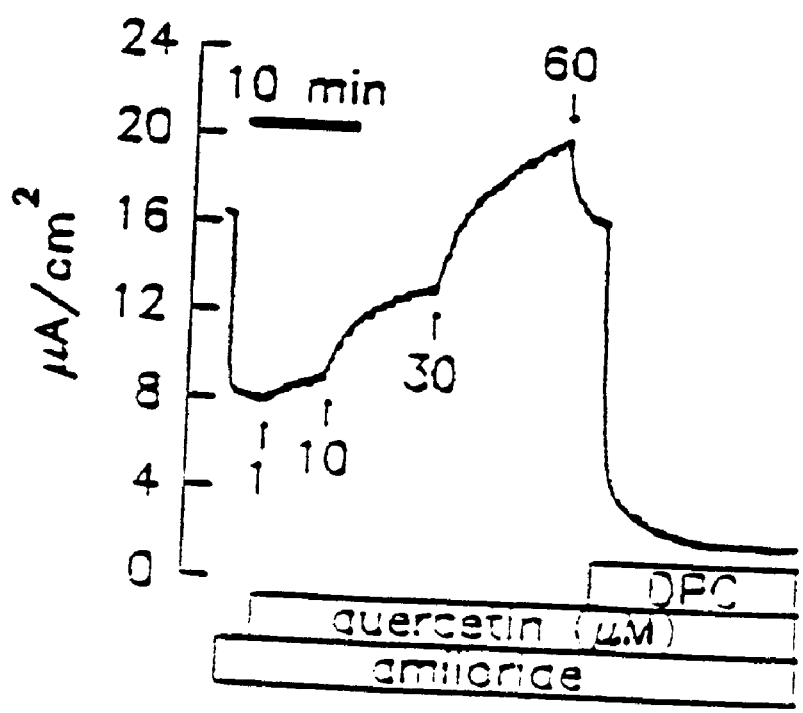
FIG. 3 is a recording illustrating the dose-dependent stimulation of transepithelial chloride secretion by quercetin (in the amounts indicated) across a primary bovine tracheal epithelium. Amiloride (50 μM) was added to block sodium transport as indicated. The CFTR channel blocker diphenylcarboxylate (DPC, 5 mM) was added as shown.

FIG. 3 illustrates the results of a related experiment to evaluate the dose-dependent stimulation of transepithelial chloride secretion by quercetin across a primary bovine tracheal epithelium. The epithelial cells were first treated with amiloride (50 $\mu$M), and then with quercetin at the indicated concentrations. The dose-response relation yielded a half maximal stimulation at 12.5 $\mu$M. At high concentrations of quercetin, the current was blocked. Current was fully inhibited by the CFTR channel blocker diphenylcarboxylate (DPC, 5 mM).

Figure 4:
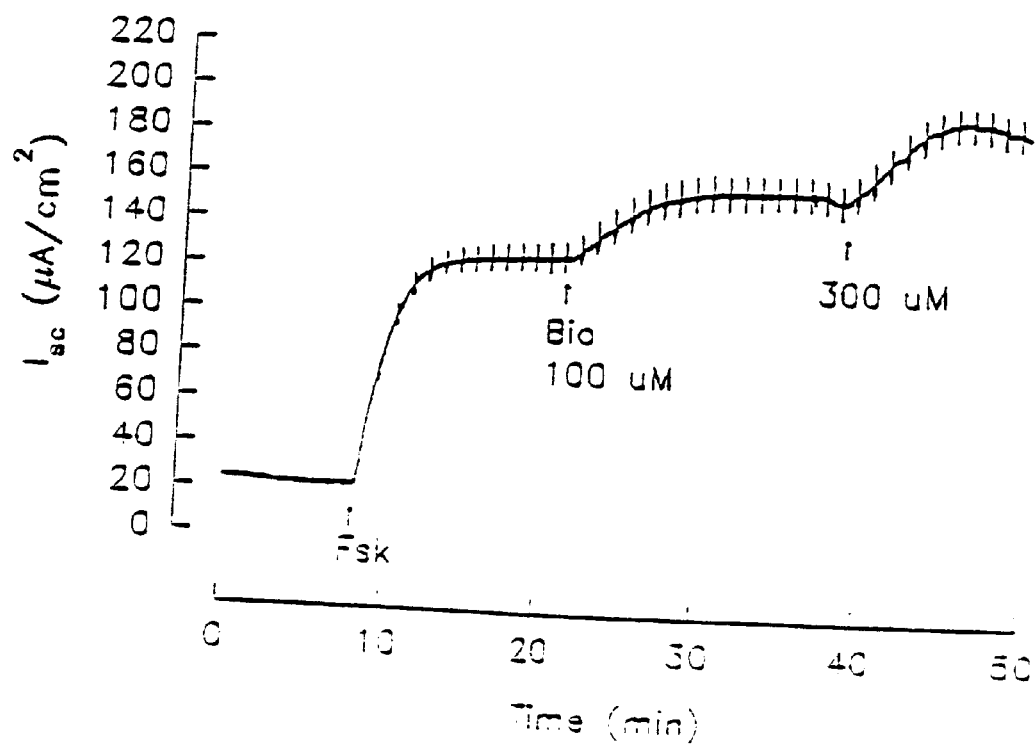
FIG. 4 is a recording showing the effect of biochanin A on transepithelial short-circuit current across a Calu-3 cell monolayer in an Ussing chamber, where the basolateral membrane was permeabilized with α-toxin and a chloride gradient was applied across the apical membrane as a driving force. The tissue was first stimulated with forskolin (Fsk, 10 μM). Subsequent addition of biochanin A (Bio, 100 and 300 μM) was subsequently added as indicated.

To evaluate the effect of biochanin A, a Calu-3 cell monolayer was prepared and permeabilized as described above. The tissue was first stimulated with forskolin (Fsk, 10 $\mu$M). The effect of biochanin A (Bio, 100 and 300 $\mu$M) on short-circuit current ($I_{sc}$) across the Calu-3 monolayer was evaluated in an Ussing chamber. As shown in FIG. 4, biochanin A further stimulated chloride secretion.

Example 2

Activation of Mutant CFTR by Representative Flavones and Isoflavones

This Example illustrates the use of the representative compounds apigenin, quercetin and genistein to activate $\Delta$F508-CFTR and G551D-CFTR in different cell types.

Figure 5:
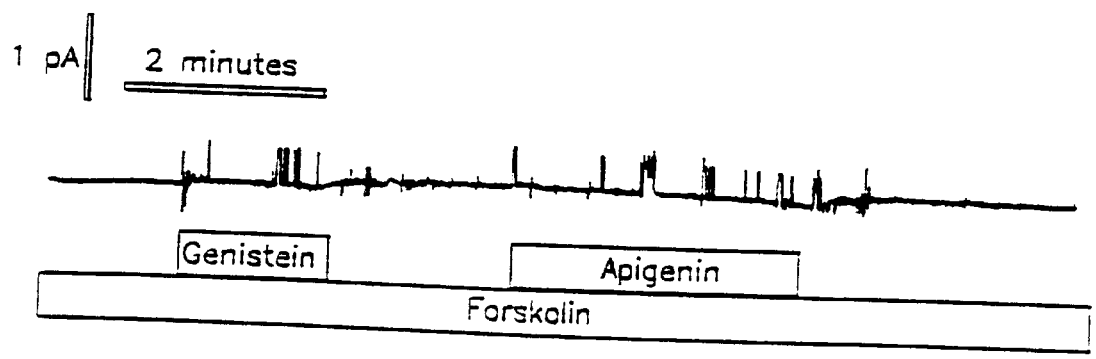
FIG. 5 is a cell-attached single channel patch clamp recording from a 3T3 cell expressing ΔF508-CFTR. The cell was treated with 10 μM forskolin as shown. Genistein (50 μM) and apigenin (50 μM), were added where indicated by boxes. The holding potential was 75 mV, and channel openings were upward.

A cell-attached single channel patch clamp recording was obtained from a 3T3 cell expressing ΔF508-CFTR as described by Hamill et al., *Pflugers Arch.* 391:85–100, 1981 and Fischer and Machen, *J. Gen. Physiol.* 104:541–566, 1994. As shown in FIG. 5, stimulation of the cell with 10 μM forskolin did not activate ΔF508-CFTR channel, but addition of genistein (50 μM) or apigenin (50 μM, where indicated by boxes) induced ΔF508-CFTR channel openings, and removal of these compounds inactivated the channels. The holding potential was 75 mV, and channel openings were upward.

Figure 6:
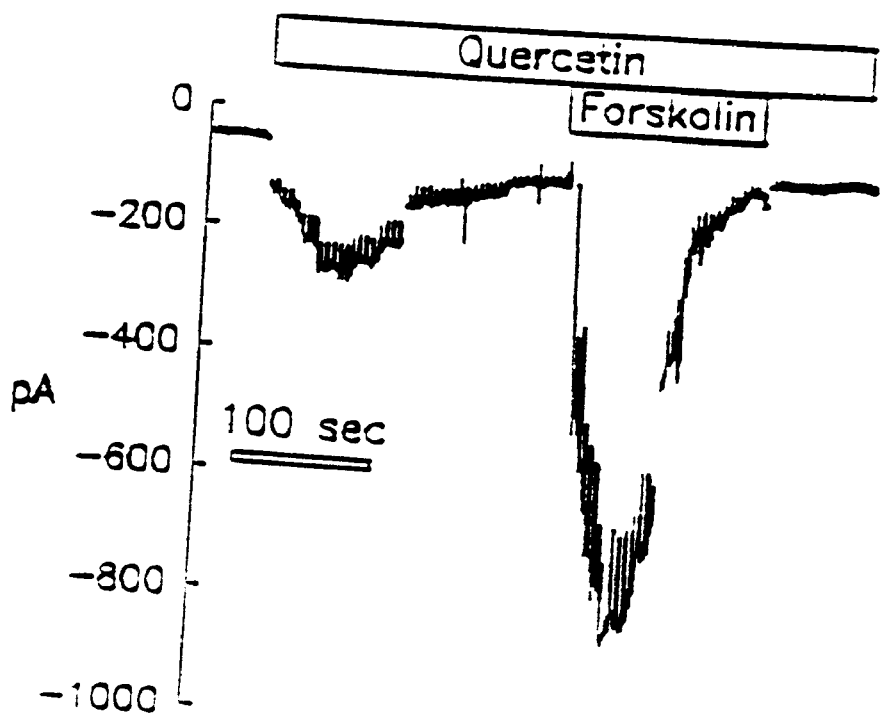
FIG. 6 is a whole cell patch clamp recording on an airway epithelial cell homozygous for ΔF508-CFTR. Before the measurement, the cell was incubated for 2 days in 5 mM 4-phenylbutyrate. 30 μM quercetin was added where indicated by the box. Further stimulation by forskolin (10 μLM) is also shown. The holding potential was −60 mV.

FIG. 6 presents a whole cell patch clamp recording on an airway epithelial cell homozygous for ΔF508-CFTR (cell type: JME cell, see Jeffersen et al., *Am. J. Physiol.* 259:L496–L505, 1990). Before the measurement, the cell was incubated for 2 days in 5 mM 4-phenylbutyrate to enhance ΔF508-CFTR expression in the plasma membrane (Rubenstein & Zeitlin, *Ped. Pulm. Suppl.* 12:234, 1995). Measurements were performed as described by Fischer et al., *J. Physiol. Lond.* 489:745–754, 1995. Addition of 30 μM quercetin activated chloride current in the whole cell mode, which was further stimulated by forskolin. The holding potential was −60 mV.

Figure 7:
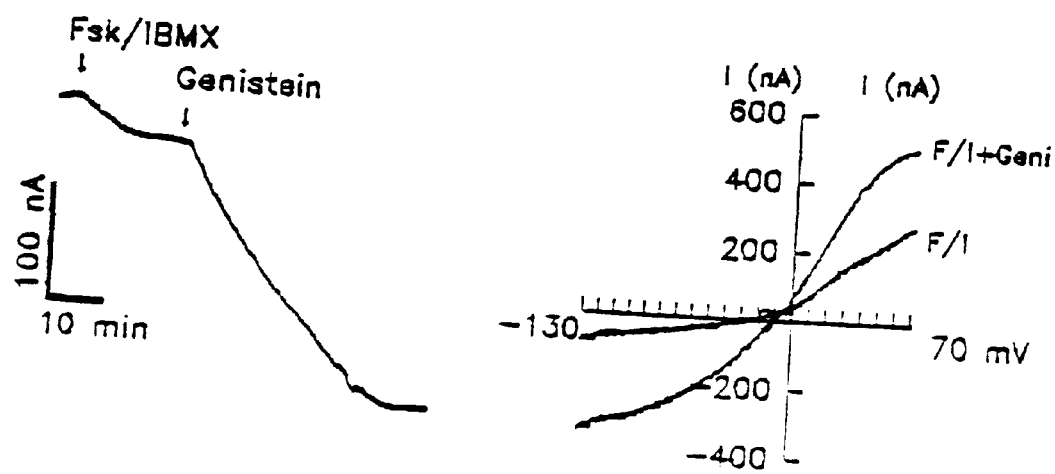
FIG. 7 is a recording illustrating the effect of genistein on G551D-CFTR expressed in a Xenopus oocyte. Current was measured with the two-electrode voltage clamp technique. G551D-CFTR was injected in oocyte. Current was first stimulated with forskolin (10 μM) and isobutylmethylxantine (IBMX; 2 mM). Genistein (50 μM) was added as indicated. The right panel shows current voltage relations recorded after treatment with forskolin and IBMX (F/I) and after treatment with genistein (F/I+Geni). A voltage ramp from −130 mV to +70 mV was applied and current was recorded during the two conditions.

The effect of genistein on chloride current in a Xenopus oocyte expressing G551D-CFTR was measured with the two-electrode voltage clamp technique (see Miledi et al., *Proc. R. Soc. Lond. Biol.* 218:481–484, 1983). G551D-CFTR (2 ng in 50 nL of water) was injected into the oocyte. Current was first stimulated with forskolin (10 μM) and isobutylmethylxantine (IBMX; 2 mM). Genistein (50 μM) was found to further activate chloride currents. As shown in FIG. 7, genistein increased conductance and shifted reversal potential to the right, which is indicative of a stimulated chloride current.

Example 3

Effect of Representative Flavones on Nasal Potential Difference

This Example illustrates the in vivo use of quercetin, apigenin and kaempferol to activate the nasal potential difference in humans and mice.

Figure 8:
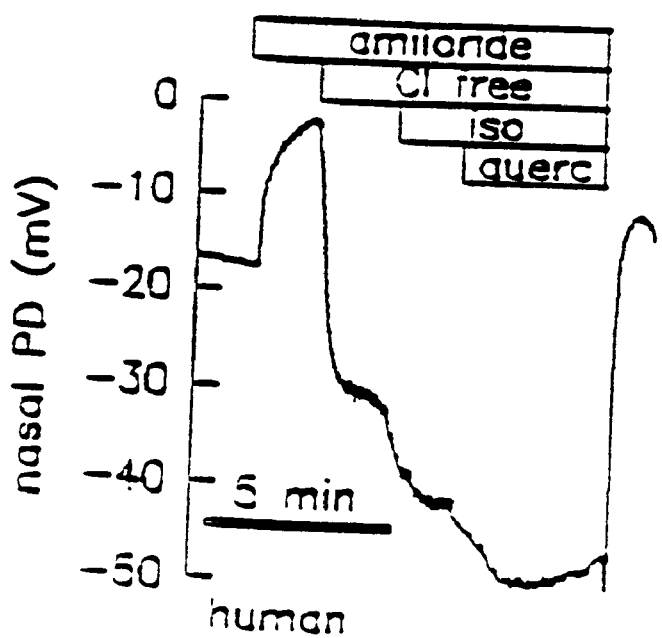
FIG. 8 is a recording illustrating the effect of quercetin on nasal potential difference (PD) measurement in a healthy human volunteer. Amiloride (50 μM) was added to block sodium transport as indicated. Conditions were rendered chloride free (Cl free) and chloride secretion was stimulated with isoproterenol (iso; 5 µM). Quercetin (querc; 10 µM) was added as indicated.
Figure 9:
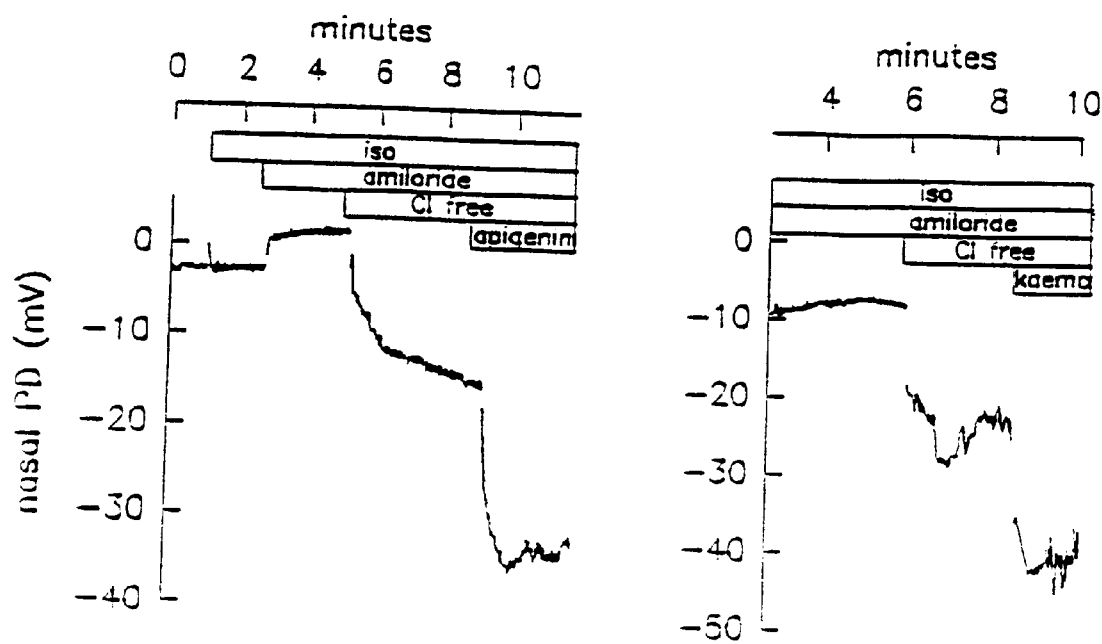
FIG. 9 is a recording illustrating the effect of apigenin and kaempferol on nasal PD in mice. Chloride secretion was stimulated with isoproterenol (iso; 5 µM), and amiloride (50 µM) was added to block sodium transport as indicated. Under chloride-free conditions (Cl free), apigenin (50 µM, left panel) and kaempferol (kaemp, 50 µM, right panel) were added as indicated.

The effect of quercetin on nasal potential difference (PD) measurement in a healthy human volunteer was measured as described by Knowles et al., *Hum. Gene Therapy* 6:445–455, 1995. Under conditions where sodium transport was blocked with amiloride (50 μM) and chloride secretion was stimulated under chloride-free conditions with isoproterenol (5 μM), quercetin (10 μM) stimulated nasal PD further (FIG. 8).

The effect of apigenin and kaempferol on nasal PD in mice was evaluated using a method similar to that employed for measurements in humans, except that a plastic tube of approximately 0.1 mm diameter was used as an exploring nasal electrode. The plastic tube was perfused with test solutions at approximately 10 μL/min. After blocking sodium transport with amiloride (50 μM) and during stimulation of chloride secretion with isoproterenol (iso;5 μM) under chloride-free conditions, apigenin (50 μM, left panel) and kaempferol (kaemp, 50 μM, right panel) further stimulated nasal PD.

These results show that the representative flavenoids quercetin, apigenin, kaempferol and biochanin A stimulate chloride transport across epithelial tissues derived from the airways in vitro, and across nasal epithelium in vivo. The results also show that the CFTR mutants ΔF508 and G551D can be activated by the representative compounds genistein and apigenin.

Example 4

Effect of Genistein on Chloride Current in Cells Expressing a Mutant CFTR

This Example illustrates the ability of the representative isoflavone genistein to activate chloride current in cells expressing a mutant CFTR.

Figure 10:
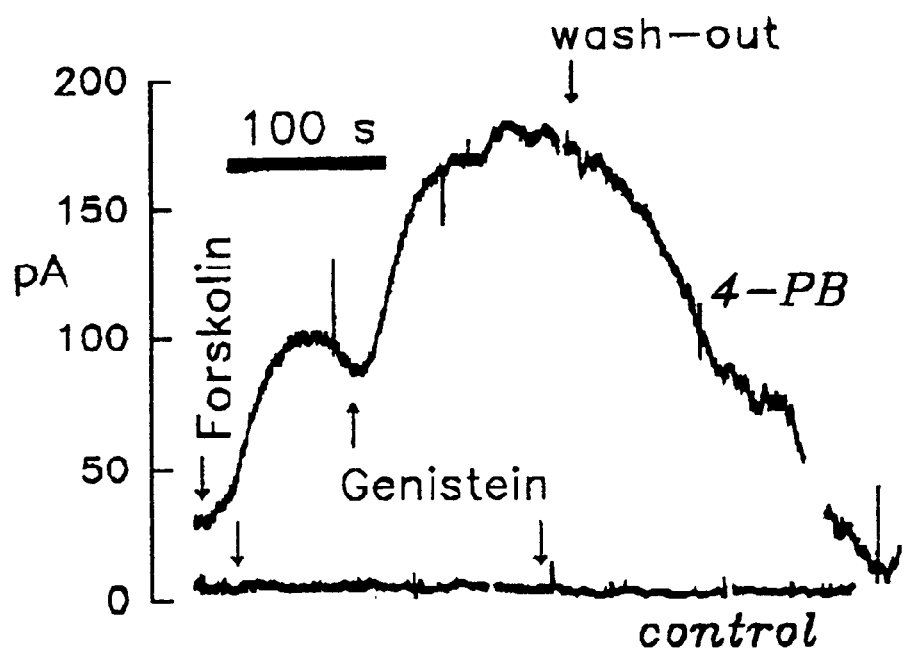
FIG. 10 is a recording illustrating the effect of genistein, with and without 4-phenylbutyrate, on chloride current in JME cells. The recording was performed at 0 mV holding potential with a 17:150 mM chloride gradient from bath to pipette. The bottom trace is from an untreated cell and the top trace is from a cell that had been incubated in 5 mM 4-phenylbutyrate (4-PB) for two days. Forskolin (10 µM) and genistein (30 µM) were added as indicated.

In one experiment, genistein was used in combination with 4-phenylbutyrate. Chloride current was measured in JME cells (human nasal epithelial cell line homozygous for the Δ508 mutation of CFTR; see Jefferson et al., *Am. J. Physiol.* 259:L496–505, 1990). The recording was performed at 0 mV holding potential with a 17:150 mM chloride gradient from bath to pipette. Under these conditions, the recorded current, shown in FIG. 10, is chloride current (Illek and Fischer, *Am. J. Physiol. (Lung Cell. Mol. Physiol.)*:L902–910, 1998). The bottom trace in FIG. 10 is from an untreated cell. Neither forskolin (10 μM nor genistein (30 μM activated current. The top tracing in FIG. 10 is from a cell that had been incubated in 5 mM 4-phenylbutyrate (4-PB) for two days (Rubenstein et al., *J. Clin. Invest.* 100:2457–2465, 1997). After 4-PB treatment, chloride current was stimulated by forskolin (by on average 30.3±19.4 pS/pF, n=6), and further activated by genistein (to an average 105±84 pS/pF) in a CF cell with the Δ508-CFTR mutation. These results further demonstrate the ability of a flavenoid compound to optimize chloride currents elicited in CF cells by other means.

Figures 11A, 11B, 11C:
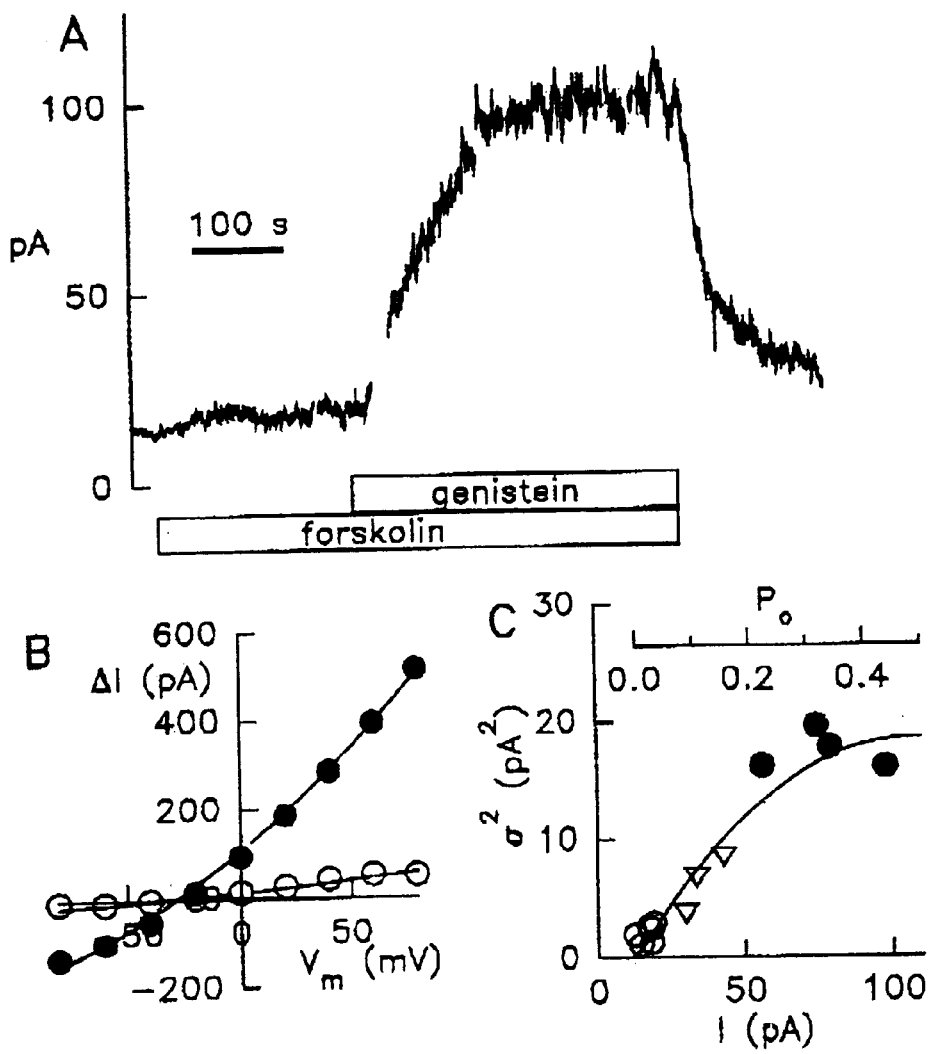
FIGS. 11A–11C are a whole cell patch clamp recording (FIG. 11A) and graphs (FIGS. 11B and 11C) illustrating the effect of forskolin and genistein on HeLa cells infected with a G551D-CFTR-containing adenovirus. Cells were stimulated with forskolin (10 µM) and genistein (30 µM), as indicated. The fit of the data with the Goldman equation is shown by the line in FIG. 11B. A current variance to mean current plot is shown in FIG. 11C.

Within another experiment, HeLa cells infected with the G551D-CFTR-containing adenovirus were investigated in the patch clamp mode. Stimulation of the cell with forskolin (10 μM) stimulated only a very small current (FIGS. 11A and 11B). On average, forskolin-stimulated conductance was 9.5±5 pS/pF (n=4). Additional stimulation with genistein (30 μM) stimulated significant chloride currents, which were time- and voltage-independent (FIG. 11B) and well fitted with the Goldman equation (line in FIG. 11B; Illek and Fischer, *Am. J. Physiol. (Lung Cell. Mol. Physiol.)* :L902–910, 1998), which are characteristics of CFTR-mediated currents. Average forskolin+genistein-activated conductance was 120±30 pS/pF (n=4). Current variance to mean current plot (FIG. 11C) were used to calculate the average open probability ($P_o$ shown on top of axis) of the population of channels carrying the total current (as described in Illek and Fischer, *Am. J. Physiol. (Lung Cell. Mol. Physiol.)*:L902–910, 1998). During forskolin stimulation, maximal $P_o$ reached was 0.04 (open circles) and after additional stimulation with genistein $P_o$ reached a maximum of 0.42 in this recording. On average, after forskolin stimulation, $P_o$=0.05±0.02 and after forskolin+genistein stimulation $P_o$=0.54±0.12. For comparison, wild type CFTR expressed in HeLa cells and recorded under the same conditions resulted in $P_o$=0.36±0.05 (n=3) after forskolin stimulation and $P_o$=0.63±0.16 after forskolin+genistein treatment.

Example 5

Effect of Representative Flavones on Nasal Potential Difference in CF Patients

This Example illustrates the in vivo use of quercetin and genistein to activate the nasal potential difference in CF patients bearing the G551D mutation.

Measurements were performed on patients as described by Alton et al., *Eur. Respir. J.* 3:922–926, 1990; Illek and Fischer, *Am. J. Physiol. (Lung Cell. Mol. Physiol.)*: L902–910, 1998; and Knowles et al., *Hum. Gene Therapy*

Figures 12A, 12B:
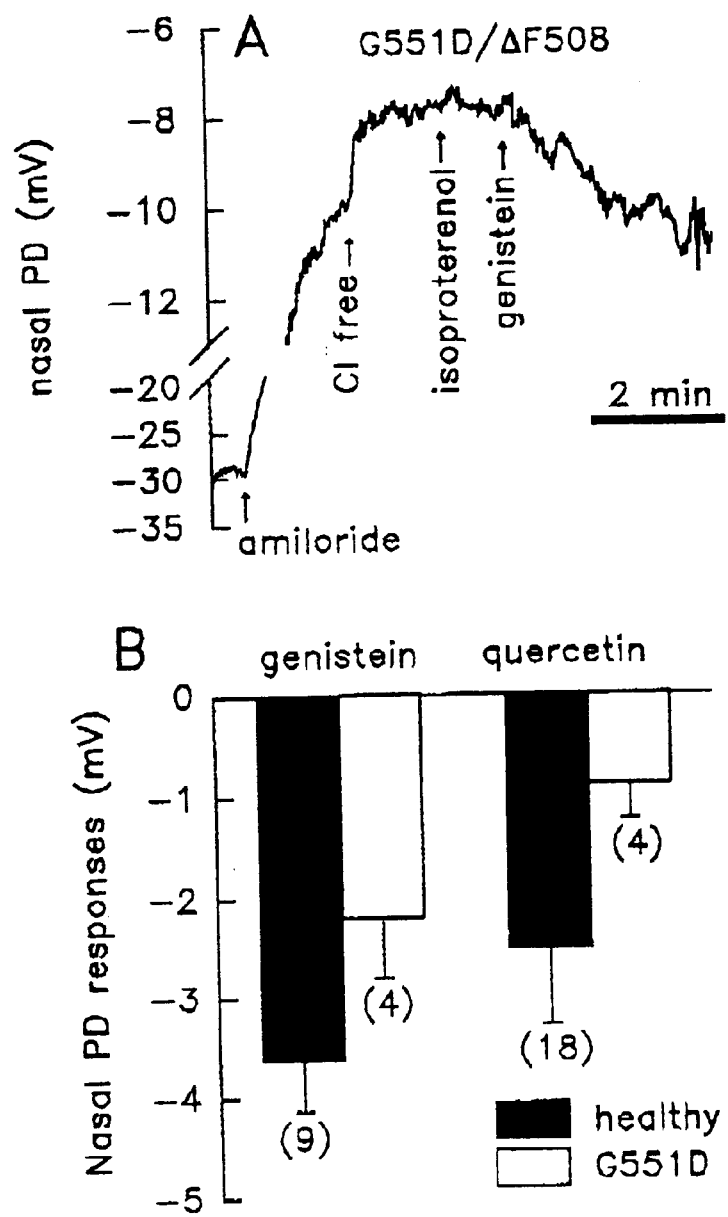
FIGS. 12A and 12B illustrate the use of representative flavenoids for the treatment of CF patients.

6:445–455, 1995). The results are presented in FIGS. 12A and 12B. FIG. 12A shows a recording from a patient with the genotype G551D/ΔF508. Initial treatment with amiloride and chloride free solution had the purpose to isolate and amplify the chloride selective potentials. Addition of the beta-adrenergic agonist isoproterenol showed no effect, which is typical for CF patients (Knowles et al., *Hum. Gene Therapy* 6:445–455, 1995). However, addition of genistein hyperpolarized nasal PD. Average responses of nasal PD to genistein and quercetin of four CF patients with the G551D mutation are shown in FIG. 12B (open bars). The filled bars show for comparison the respective responses in healthy subjects. The genotypes of the 4 CF patients were: two G551D/ΔF508, one G551D/G551D and one G551D/unknown. Responses are most likely due to the G551D mutation because the homozygous G551D patient responded not different compared to the heterozygous G551D patients. Genistein and quercetin responses of nasal PD in CF patients were significant ($p<0.05$).

These results demonstrate that CFTR mutations are sensitive to flavenoid treatment, and provide additional evidence for therapeutic benefit of such compounds for the treatment of cystic fibrosis.

Example 6

Effect of Additional Representative Polyphenolic Compounds on Epithelial Cell Chloride Currents This Example illustrates the effect of further flavenoids and isoflavenoids on chloride currents in airway epithelial cells.

Figure 13A:
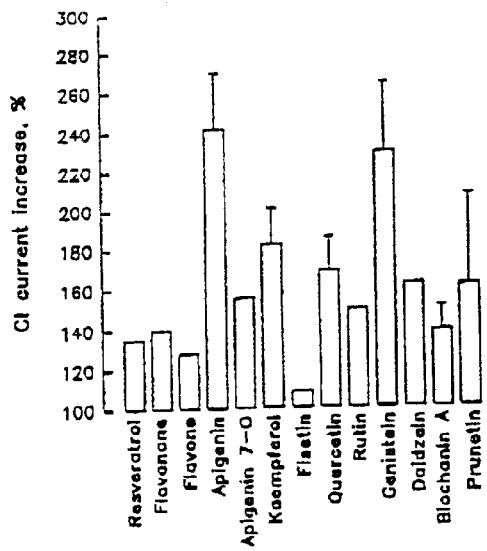
FIGS. 13A–13C illustrate the effect of additional representative flavenoids and isoflavenoids on chloride current in epithelial cells.

Airway epithelial cells were prestimulated with 10 μM forskolin. The percent increase in chloride current was then determined following treatment with a series of polyphenolic compounds. FIG. 13A summarizes the stimulatory effect of these compounds. On average, chloride currents were further stimulated by reservatrol (100 μM) to 135%, by flavanone (100 μM) to 140%, by flavone (200 μM) to 128%, by apigenin (20 μM) to 241%, by apigenin 7-O-neohesperidoside (30 μM) to 155%, by kaempferol (20 μM) to 182%, by fisetin (100 μM) to 108%, by quercetin (30 μM) to 169%, by rutin (30 μM) to 149%, by genistein (30 μM) to 229%, by daidzein (50 μM) to 162%, by biochanin A (100 μM) to 139% and by prunetin (100 μM) to 161%.

Figure 13B:
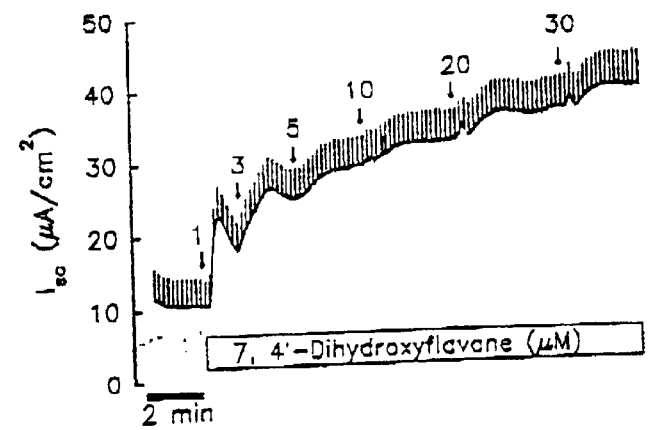

The stimulatory effect of 7,4' Dihydroxyflavone is shown in FIG. 13B. Addition of 7,4'-Dihydroxyflavone to the mucosal perfusion dose-dependently stimulated transepithelial Cl currents in unstimulated Calu-3 monolayers. This experiment was performed using unstimulated tissue.

Figure 13C:
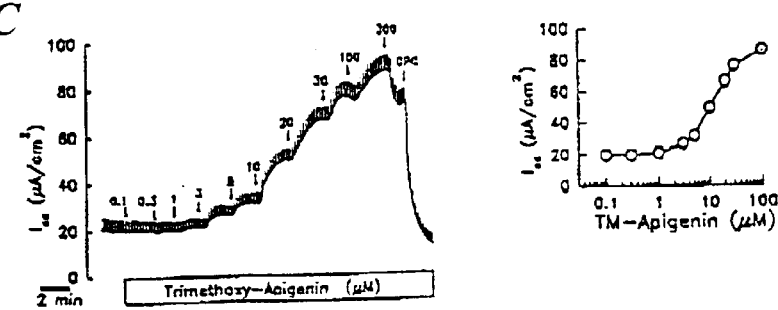

The stimulatory effect of trimethoxy-apigenin is shown in FIG. 13C. Addition of trimethoxy-apigenin to the mucosal perfusion dose-dependently stimulated transepithelial Cl currents in unstimulated Calu-3 monolayers. Kinetic analysis is depicted on the right panel and estimated half maximal stimulatory dose was 11.7 μM.

These results indicate that a variety of polyphenolic compounds stimulate chloride currents in epithelial cells.

Example 7

Effect of Reservatrol on Chloride Currents

This Example illustrates the stimulatory effect of reservatrol on transepithelial chloride currents.

Figure 14:
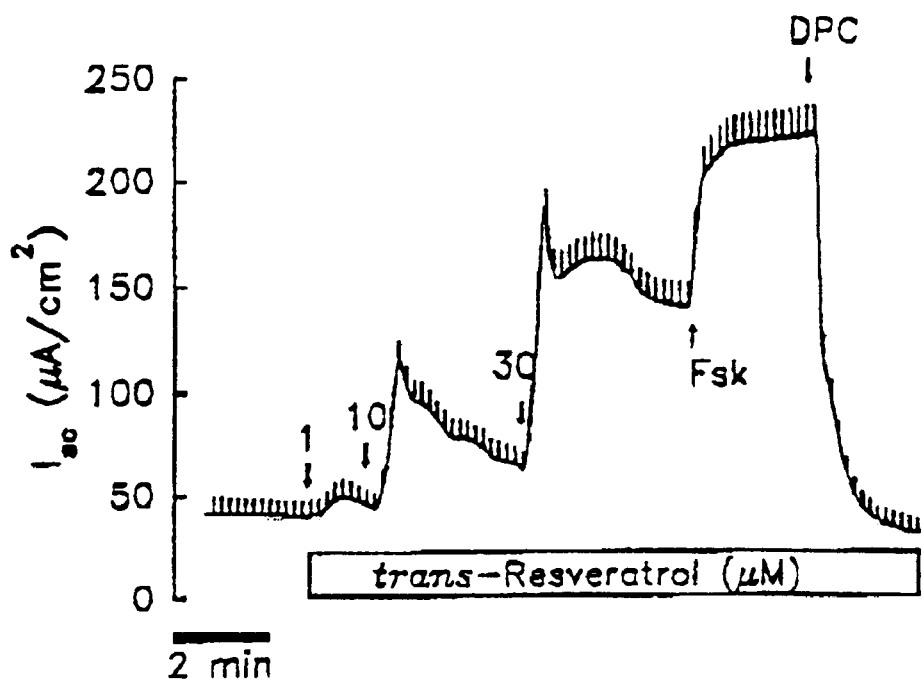
FIG. 14 is a recording illustrating the dose-dependent stimulation of transepithelial short-circuit current (Isc) across Calu-3 monolayers by reservatrol. Increasing concentrations of reservatrol (as indicated in µM) were added to the mucosal perfusion and dose-dependently increased chloride currents. For comparison, currents were further stimulated by serosal addition of 20 µM forskolin. Stimulated chloride current was completely blocked by addition of the chloride channel blocker DPC (5 mM). Currents were recorded with a serosal-to-mucosal chloride gradient at 0 mV and pulses were obtained at 2 mV.

Unstimulated Calu-3 monolayers were treated with increasing concentrations of reservatrol. FIG. 14 shows the recording generated following the addition of reservatrol to the mucosal perfusion dose-dependently stimulated transepithelial chloride currents in unstimulated Calu-3 monolayers. For comparison, currents were further stimulated by serosal addition of forskolin. The stimulated chloride current was completely blocked by the Cl channel blocker DPC. These results indicate that reservatrol stimulates transepithelial chloride transport.

Example 8

Effect of Ascorbic Acid and Dehydroascorbic Acid on Chloride Currents

This Example illustrates the stimulatory effect of ascorbic acid and dehydroascorbic acid on transepithelial chloride current.

Figure 15:
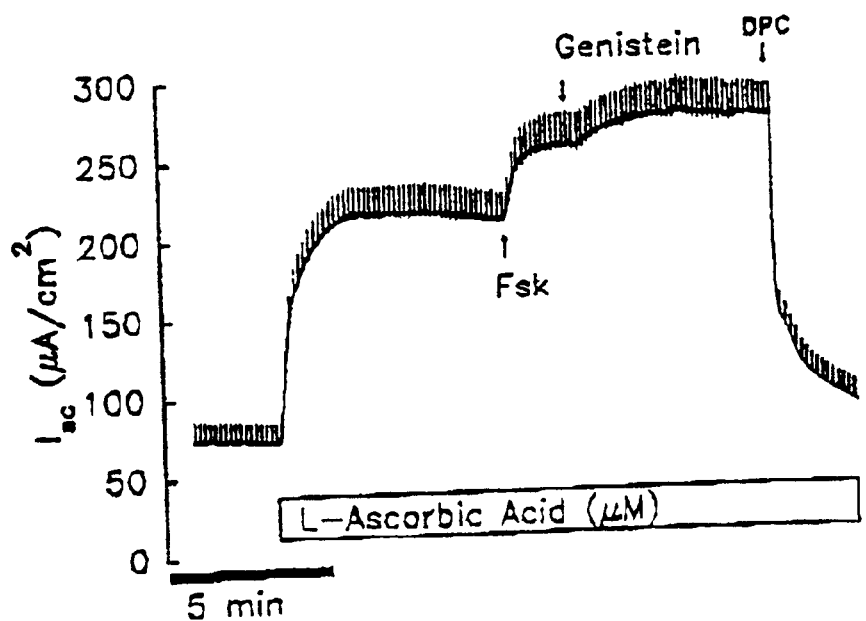
FIG. 15 is a recording showing L-ascorbic acid and genistein stimulation of transepithelial short-circuit current (Isc) across Calu-3 monolayers. Ascorbic acid (100 µM) was added as indicated. For comparison, ascorbic acid-stimulated chloride current was subsequently stimulated by the cAMP elevating agonist forskolin (20 µM, serosal). The CFTR activator genistein (20 mM) was then added to the mucosal perfusion as indicated. Stimulated current was completely blocked by addition of the chloride channel blocker DPC (5 mM), added as indicated. Currents were recorded with a serosal-to-mucosal chloride gradient at 0 mV and pulses were obtained at 2 mV.

Unstimulated Calu-3 monolayers were stimulated with L-ascorbic acid, as shown in FIG. 15. Addition of L-ascorbic acid to the mucosal or serosal perfusion very effectively stimulated transepithelial chloride secretion in unstimulated Calu-3 monolayers. For comparison, chloride currents were further stimulated by serosal addition of forskolin. In the continued presence of L-ascorbic acid and forskolin, it is remarkable that addition of genistein further stimulated chloride currents. These results indicate that genistein serves as a potent drug that is able to hyperstimulate chloride secretion and thereby maximize chloride transport across epithelia. The stimulated chloride current was completely blocked by the chloride channel blocker DPC.

Figure 16:
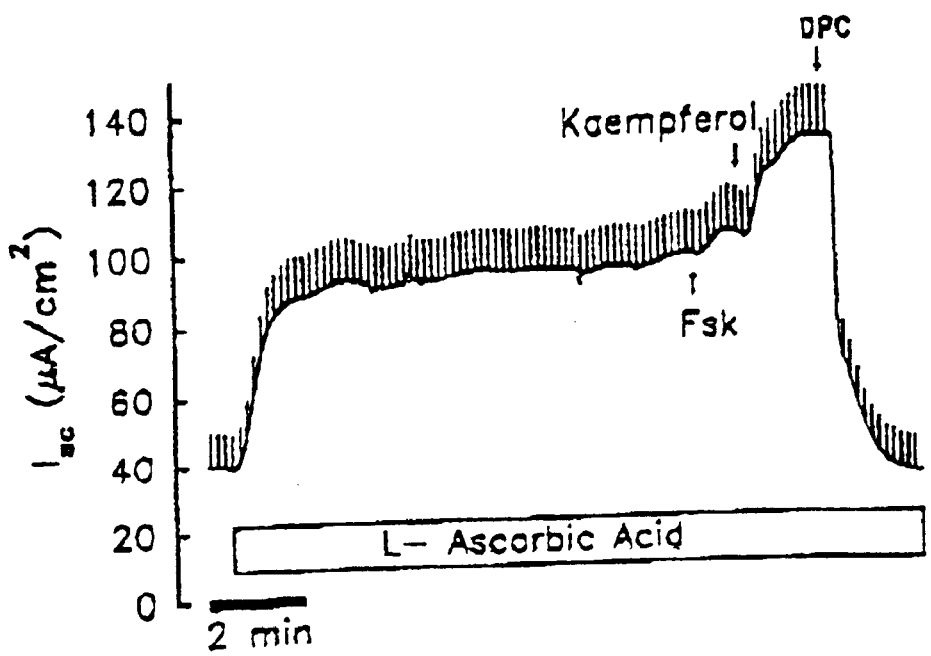
FIG. 16 is a recording showing L-Ascorbic acid and kaempferol stimulation of transepithelial short-circuit current (Isc) across Calu-3 monolayers. 100 µM ascorbic acid and forskolin (fsk, 20 µM, serosal) were added as indicated. The CFTR activator kaempferol (20 µM) was subsequently added, as indicated. Stimulated current was completely blocked by addition of the chloride channel blocker DPC (5 mM). Currents were recorded with a serosal-to-mucosal chloride gradient at 0 mV and pulses were obtained at 2 mV.

The stimulatory effect of L-ascorbic acid is also shown in FIG. 16. Addition of 100 μM L-ascorbic acid to the mucosal or serosal perfusion very effectively stimulated transepithelial chloride currents in unstimulated Calu-3 monolayers. For comparison, ascorbic acid-stimulated chloride currents were stimulated by the cAMP elevating agonist forskolin (20 μM, serosal). Under these stimulated conditions kaempferol further hyperstimulated chloride currents. The stimulated chloride current was completely blocked by the chloride channel blocker DPC (5 mM).

Figure 18:
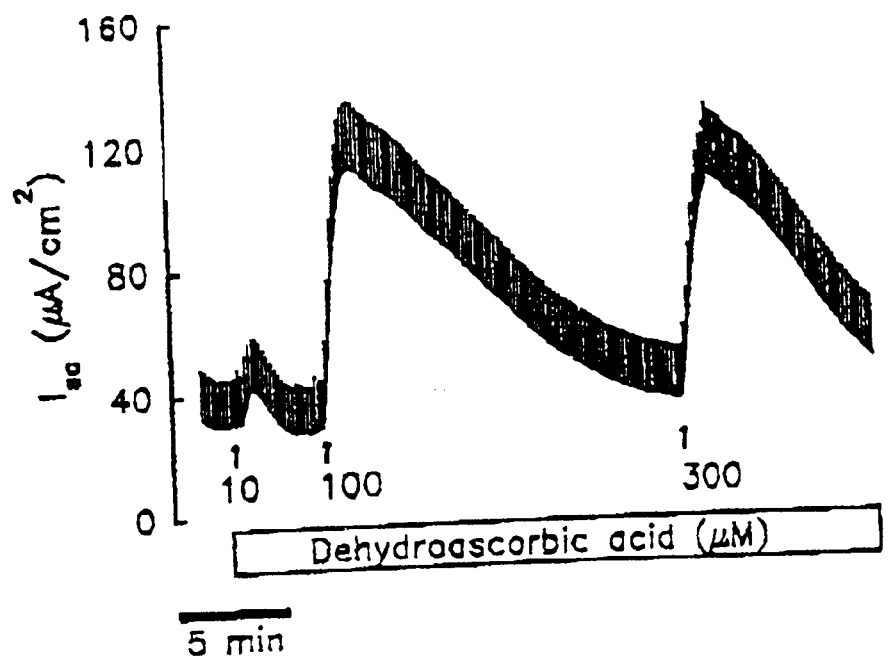
FIG. 18 is a recording illustrating the stimulation of transepithelial short-circuit current (Isc) across Calu-3 monolayers by addition of 10, 100 and 300 µM dehydroascorbic acid. Currents were recorded with a serosal-to-mucosal chloride gradient at 0 mV and pulses were obtained at 2 mV.

The stimulatory effect of dehydroascorbic acid is shown in FIG. 18. Addition of dehydroascorbic acid at 10, 100 or 300 μM to the mucosal and serosal perfusion effectively stimulated transepithelial chloride currents in unstimulated Calu-3 monolayers. Stimulated Cl currents returned to baseline after 5–15 min.

Example 9

Effect of Ascorbic Acid on Chloride Currents in vivo

This Example illustrates the stimulatory effect of ascorbic acid on human nasal potential difference.

Figure 17:
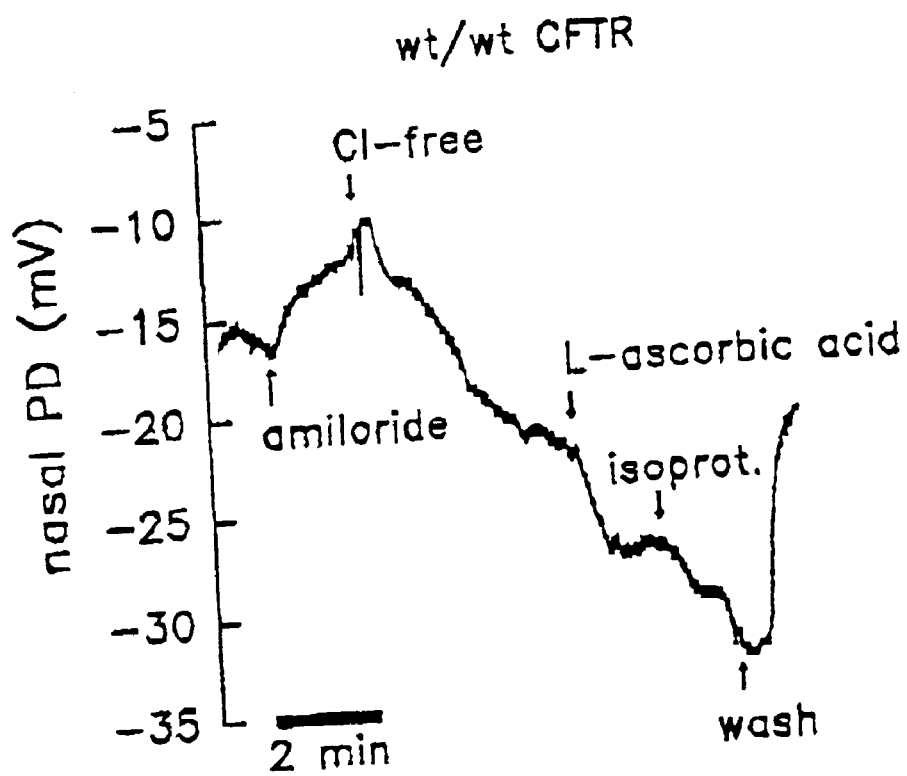
FIG. 17 is a recording illustrating the effect of L-ascorbic acid on nasal potential difference in human subjects. Amiloride, chloride-free solution and L-ascorbic acid (100 µM) were added to the luminal perfusate in the nose, as indicated. The β-adrenergic agonist isoproterenol was also added as indicated. Stimulation was reversed by washing out drugs with NaCl Ringer solution.

Nasal potential difference measurement was performed on a human volunteer according to a protocol by Knowles et al., *Hum. Gene Therapy* 6:445–455, 1995. Addition of L-ascorbic acid (100 μM) to the luminal perfusate in the nose (in the presence of amiloride (blocks Na currents) and in chloride-free solution) hyperpolarized nasal potential difference (PD) by 6.3 mV (FIG. 17). Addition of the β-adrenergic agonist isoproterenol further hyperpolarized nasal PD. Stimulation was reversed by washing out drugs with NaCl Ringer solution. These results demonstrate the ability of ascorbic acid to stimulate chloride transport in epithelia in humans.

Example 10

Effect of Genistein on Chloride Currents in Mammary Epithelia

This Example illustrates the stimulatory effect of genistein in mammary epithelial cells.

Figure 19:
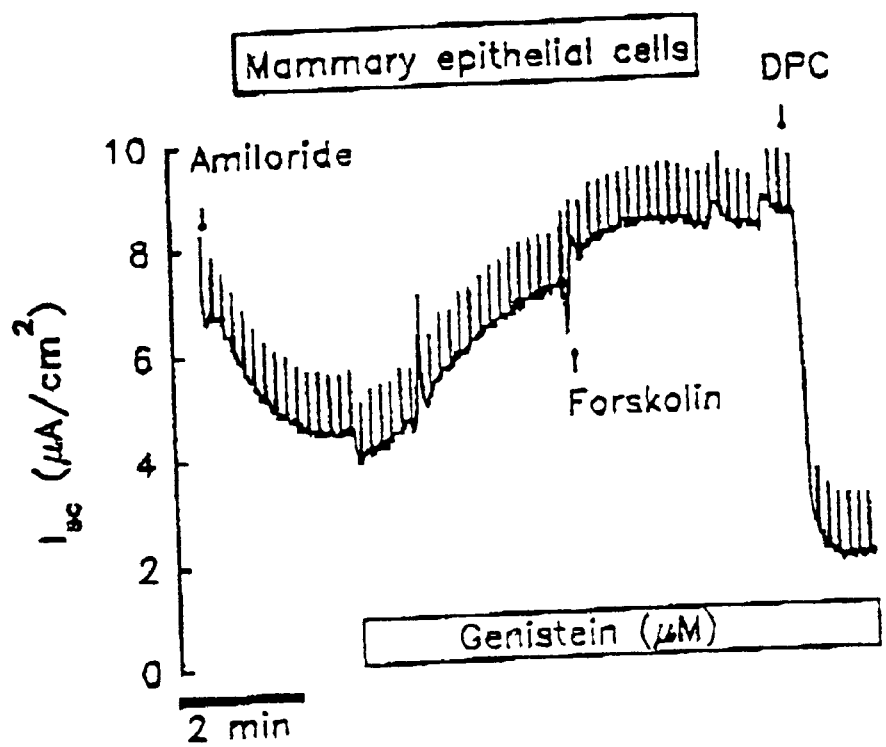
FIG. 19 is a recording illustrating the stimulatory effect of 20 µM genistein on transepithelial short-circuit current (Isc) across 31EG4 mammary epithelial monolayers. Na currents were blocked by mucosal addition of amiloride (10 mM), and chloride currents were further stimulated by forskolin (20 µM, serosal), as indicated. Currents were recorded in symmetrical NaCl Ringers solution at 0 mV and pulses were obtained at 2 mV.

The stimulation of transepithelial short-circuit current (Isc) across 31EG4 mammary epithelial monolayers by addition of 20 μM genistein is shown in FIG. 19. Na currents were blocked by mucosal addition of amiloride (10 mM). Chloride currents were further stimulated by forskolin (20 μM, serosal). Currents were recorded in symmetrical NaCl Ringers solution at 0 mV and pulses were obtained at 2 mV.

From the foregoing, it will be appreciated that, although specific embodiments of the invention have been described herein for the purpose of illustration, various modifications may be made without deviating from the spirit and scope of the invention. Accordingly, the invention is not limited except as by the appended claims.

What is claimed is:

1. A method for enhancing chloride transport in epithelial cells, comprising contacting epithelial cells with a compound capable of stimulating chloride transport, wherein the compound is not genistein and wherein the compound is:

(a) a polyphene compound having the formula:

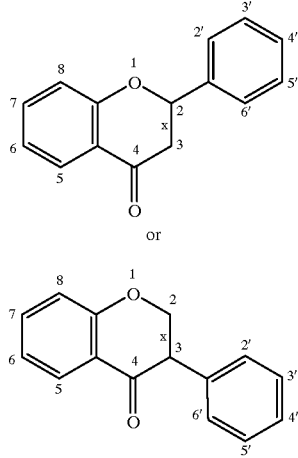

or wherein carbon atoms at positions 2, 3, 5, 6, 7, 8, 2', 3', 4', 5' and 6' are bonded to a moiety independently selected from the group consisting of hydrogen atoms, hydroxyl groups and methoxyl groups, and wherein X is a single bond or a double bond; or (b) a stereoisomer of any of the foregoing polyphenolic compounds.

2. A method according to claim 1, wherein the compound is selected from the group consisting of flavanone, flavone, dihydroxyflavone, trimethoxy-apigenin, apigenin 7-O-neohesperidoside, fisetin, rutin, daidzein and prunetin.

3. A method for enhancing chloride transport in epithelial cells, comprising contacting epithelial cells with a compound selected from the group consisting of reservatrol, ascorbic acid, ascorbate salts and dehydroascorbic acid.

4. A method according to claim 1 or claim 3, wherein the epithelial cells are airway epithelial cells.

5. A method according to claim 4, wherein the airway epithelial cells are present in a mammal.

6. A method according to claim 5, wherein the compound is administered orally.

7. A method according to claim 5, wherein the compound is administered by inhalation.

8. A method according to claim 1 or claim 3, wherein the epithelial cells are intestinal cells.

9. A method according to claim 8, wherein the intestinal epithelial cells are present in a mammal.

10. A method according to claim 9, wherein the compound is administered orally.

11. A method according to claim 1 or claim 3, wherein the epithelial cells are pancreas, gallbladder, sweat duct, salivary gland or mammary epithelial cells.

12. A method according to claim 11, wherein the intestinal epithelial cells are present in a mammal.

13. A method according to claim 1 or claim 3, wherein the cells are further contacted with a substance that increases (a) trafficking of a CFTR to the plasma membrane of the cells; and/or (b) expression of a CFTR in the cells.

14. A method according to claim 1 or claim 3, wherein the compound is present within a pharmaceutical composition comprising a physiologically acceptable carrier or excipient.

15. A method according to claim 1 or claim 3, wherein the epithelial cells produce a mutated CFTR protein.

16. A method according to claim 15, wherein the mutated CFTR protein has a point mutation at position 551.

17. A method according to claim 1 or claim 3, wherein the pharmaceutical composition further comprises a substance that increases (a) trafficking of a CFTR to the plasma membrane of the cells; and/or (b) expression of a CFTR in the cells.

18. A method according to claim 17, wherein the substance increases expression of a CFTR in the cells and is 4-phenylbutyrate or sodium butyrate.

19. A method according to claim 17, wherein the substance is a chemical chaperone that increases trafficking of a CFTR to the plasma membrane of the cells, and wherein the compound is selected from the group consisting of glycerol, dimethylsulfoxide, trimethylamine N-oxide, taurin, methylamine and deoxyspergualin.

20. A method according to claim 1, wherein the cells are further contacted with a compound selected from the group consisting of reservatrol, ascorbic acid, ascorbate salts and dehydroascorbic acid.

21. A method according to claim 20, wherein the cells are contacted with a polyphenolic compound and ascorbic acid.

22. A method according to claim 21, wherein the polyphenolic compound is daidzein or prunetin.

23. A method for enhancing chloride transport in epithelial cells, comprising contacting epithelial cells with genistein, wherein the epithelial cells produce a mutated CFTR protein.

24. A method according to claim 23, wherein the mutated CFTR protein is G551D-CFTR or ΔF508-CFTR.

25. A method according to claim 23, wherein the epithelial cells are further contacted with a substance that increases (a) trafficking of a CFTR to the plasma membrane of the cells; and/or (b) expression of a CFTR in the cells.

26. A method according to claim 25, wherein the substance increases expression of a CFTR in the cells and is 4-phenylbutyrate or sodium butyrate.

27. A method according to claim 25, wherein the substance is a chemical chaperone that increases trafficking of a CFTR to the plasma membrane of the cells, and wherein the compound is selected from the group consisting of glycerol, dimethylsulfoxide, trimethylamine N-oxide, taurin, methylamine and deoxyspergualin.

28. A method for enhancing chloride transport in epithelial cells, comprising contacting epithelial cells with genistein and a compound selected from the group consisting of reservatrol, ascorbic acid, ascorbate salts and dehydroascorbic acid.

29. A method for increasing chloride ion conductance in airway epithelial cells of a patient afflicted with cystic fibrosis, wherein the patient's CFTR protein has a mutation at position 551, the method comprising administering to a mammal one or more compounds selected from the group consisting of flavones and isoflavones, wherein the compound is capable of stimulating chloride secretion.

30. A method according to claim 29, wherein the compound is genistein.

31. A method according to claim 29, wherein the compound is quercetin.

32. A pharmaceutical composition for treatment of cystic fibrosis, comprising:

(a) one or more flavones or isoflavones capable of stimulating chloride secretion;

(b) one or more of:
    (i) a compound that increases expression of a CFTR in an epithelial cell; and/or
    (ii) a chemical chaperone that increases trafficking of a CFTR to a plasma membrane in an epithelial cell; and (c) a physiologically acceptable carrier.

* * * * *

UNITED STATES PATENT AND TRADEMARK OFFICE
CERTIFICATE OF CORRECTION

| | |
|---|---|
| PATENT NO. | : 6,329,422 B1 |
| APPLICATION NO. | : 09/174077 |
| DATED | : December 11, 2001 |
| INVENTOR(S) | : Fischer et al. |

It is certified that error appears in the above-identified patent and that said Letters Patent is hereby corrected as shown below:

<u>Column 57 Claim 1</u>
Line 23, "polyphene" should read as --polyphenolic--.

Signed and Sealed this

Twenty-first Day of July, 2009

JOHN DOLL
*Acting Director of the United States Patent and Trademark Office*